United States Patent [19]
Moro et al.

[11] Patent Number: 5,292,515
[45] Date of Patent: Mar. 8, 1994

[54] MANUFACTURE OF WATER-SWELLABLE HYDROPHILIC ARTICLES AND DRUG DELIVERY DEVICES

[75] Inventors: Daniel G. Moro, Randolph; Petr Kuzma, Monmouth Junction; Harry Quandt, North Middletown, all of N.J.

[73] Assignee: Hydro Med Sciences, a Division of National Patent Development Corporation, New York, N.Y.

[21] Appl. No.: 41,523

[22] Filed: Mar. 31, 1993

Related U.S. Application Data

[63] Continuation of Ser. No. 589,957, Sep. 28, 1990, abandoned.

[30] Foreign Application Priority Data

Oct. 5, 1992 [EP] European Pat. Off. ....... 92 300394.1

[51] Int. Cl.$^5$ ............................................. A61M 5/178
[52] U.S. Cl. ............................ 424/422; 424/423; 264/310; 264/311; 264/255; 264/267; 604/59
[58] Field of Search ............... 604/57, 59, 60, 64; 264/255, 267, 310, 311; 424/473, 422, 423

[56] References Cited

U.S. PATENT DOCUMENTS

| | | | |
|---|---|---|---|
| 2,513,014 | 6/1950 | Fields | 604/60 |
| 3,921,632 | 11/1975 | Bardani | 604/60 |
| 4,846,793 | 7/1989 | Leonard | 604/60 |
| 4,871,094 | 4/1988 | Gall | 604/59 |
| 4,959,217 | 9/1990 | Sanders | 424/473 |
| 4,994,028 | 2/1991 | Leonard | 604/59 |
| 5,004,614 | 4/1991 | Staniforth | 424/78 |
| 5,035,891 | 7/1991 | Runkel | 424/473 |

FOREIGN PATENT DOCUMENTS

| | | |
|---|---|---|
| 0246653 | 11/1987 | European Pat. Off. . |
| 0384646 | 8/1990 | European Pat. Off. . |
| 821383 | 12/1937 | France . |
| 1306541 | 2/1973 | United Kingdom . |

*Primary Examiner*—Thurman K. Page
*Assistant Examiner*—Raj Bawa
*Attorney, Agent, or Firm*—Howson and Howson

[57] ABSTRACT

A method of preparing a hydrophilic plastic cartridge by centrifugally casting polymerizable hydrophilic material in a rotating polymerization tube whose longitudinal axis is maintained parallel to the ground. The speed of rotation causes radial outward displacement of the polymerizable material which upon assuming a predetermined shape within the rotating tube is then polymerized to the predetermined solid configuration. The resulting plastic cartridge is characterized by smooth, unscored internal and external cylindrical surfaces. The cartridges are used as a rate-limiting membrane in drug delivery devices. Sterilized kits containing a disposable needle/syringe or trocar-like instrument and the drug delivery device are used for subcutaneous implantation of the device in an animal body.

42 Claims, 11 Drawing Sheets

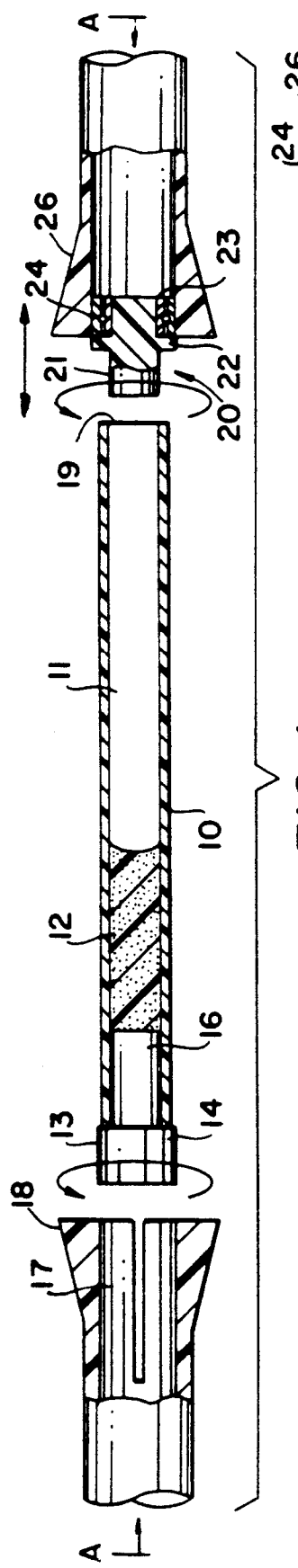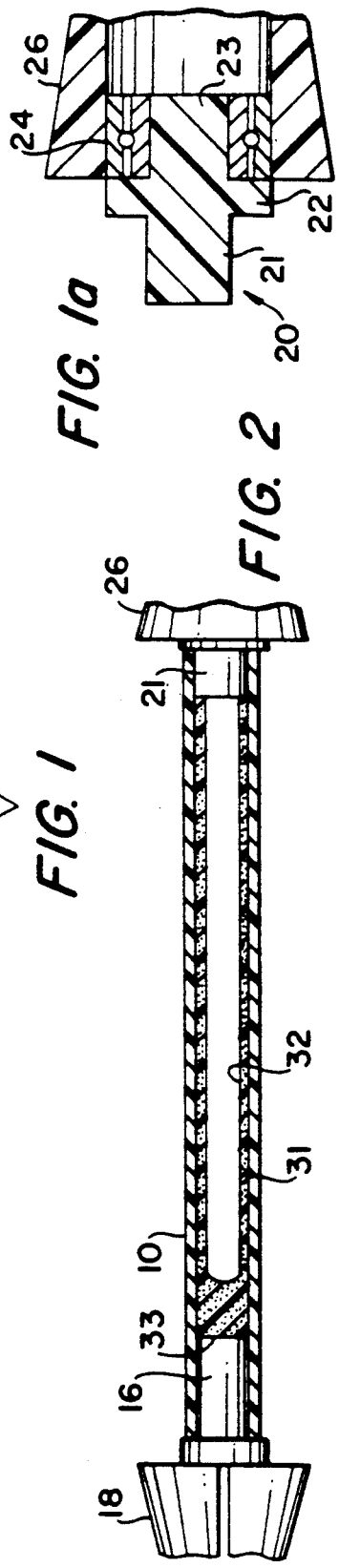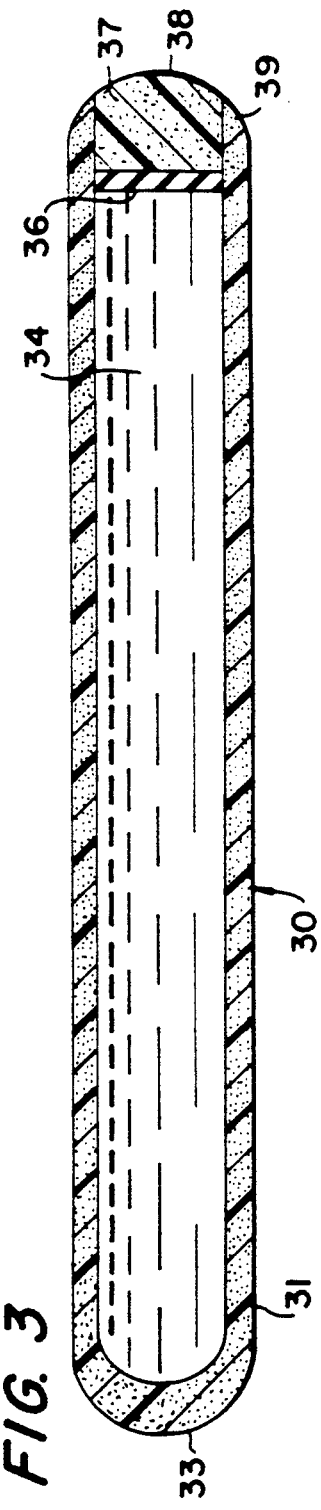
FIG. 1
FIG. 1a
FIG. 2
FIG. 3

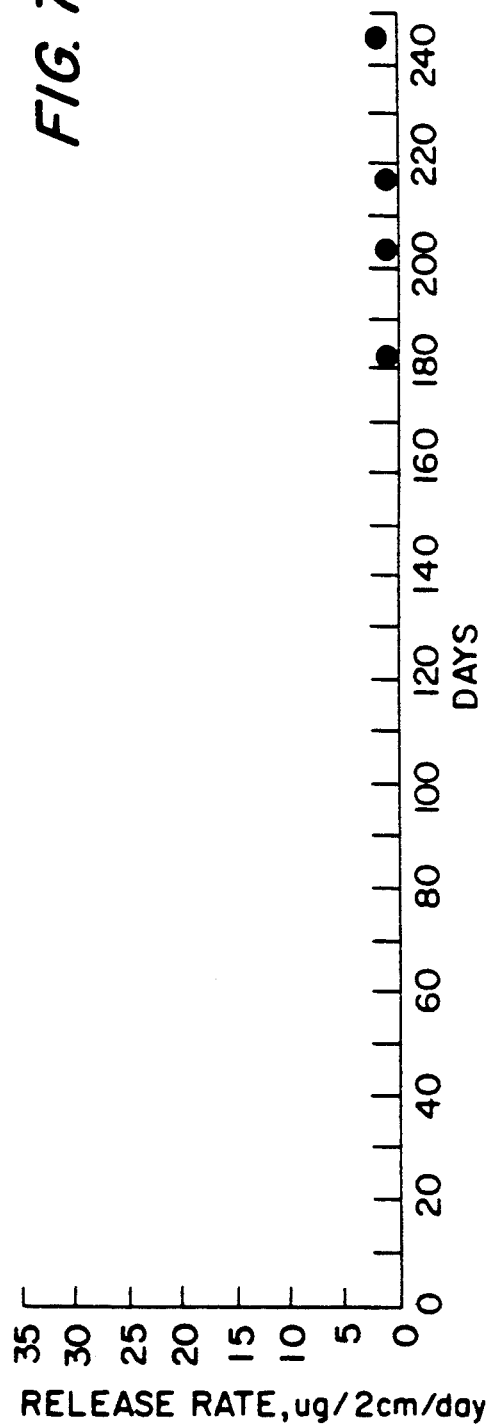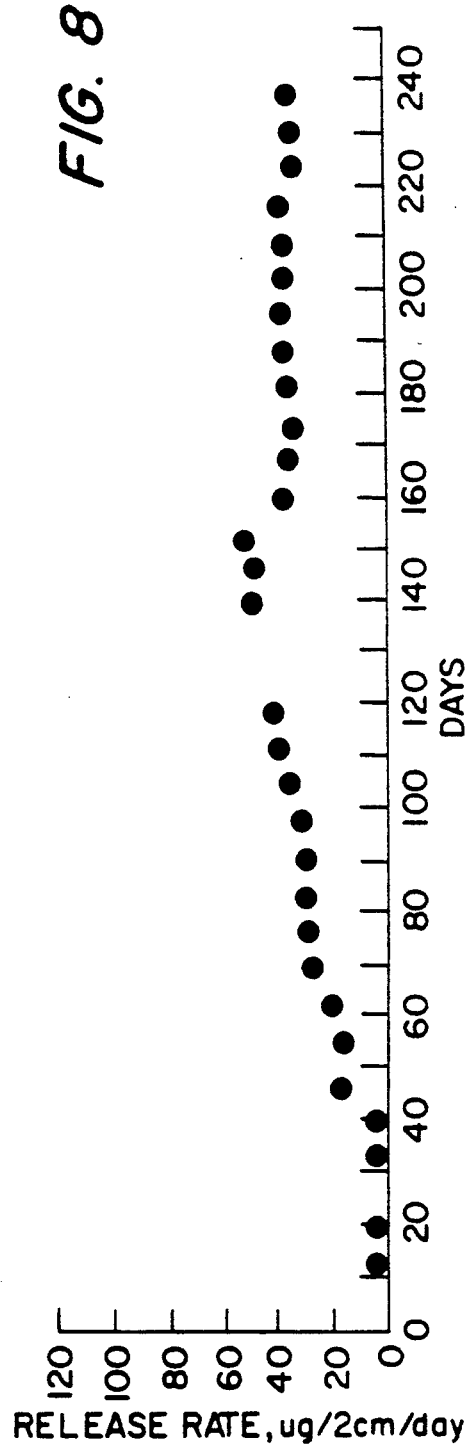

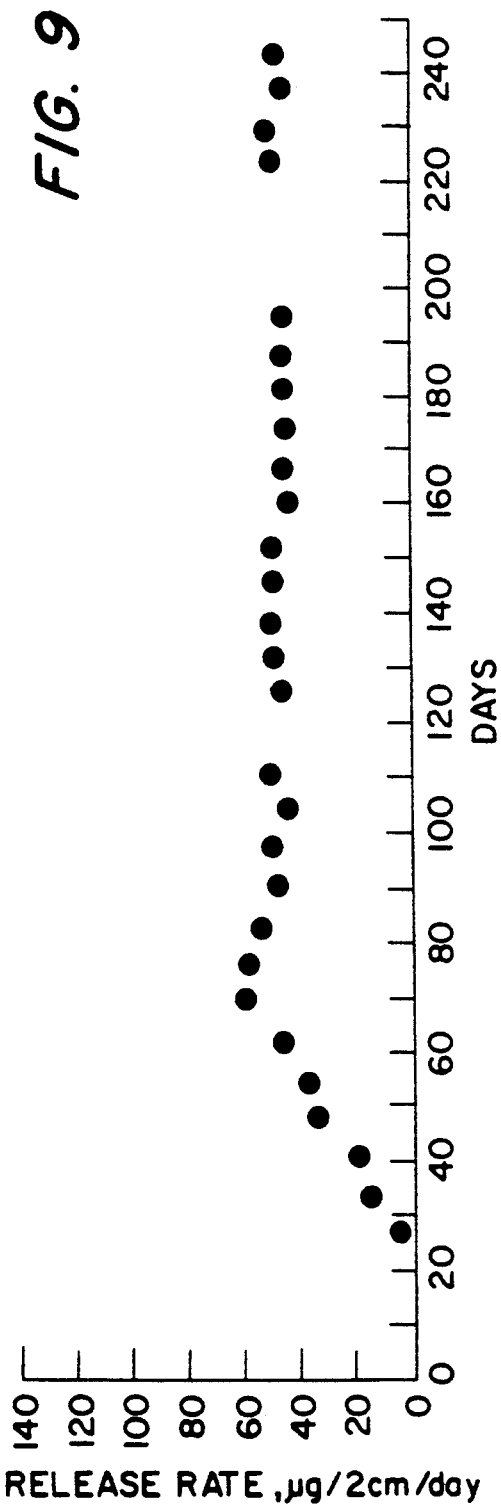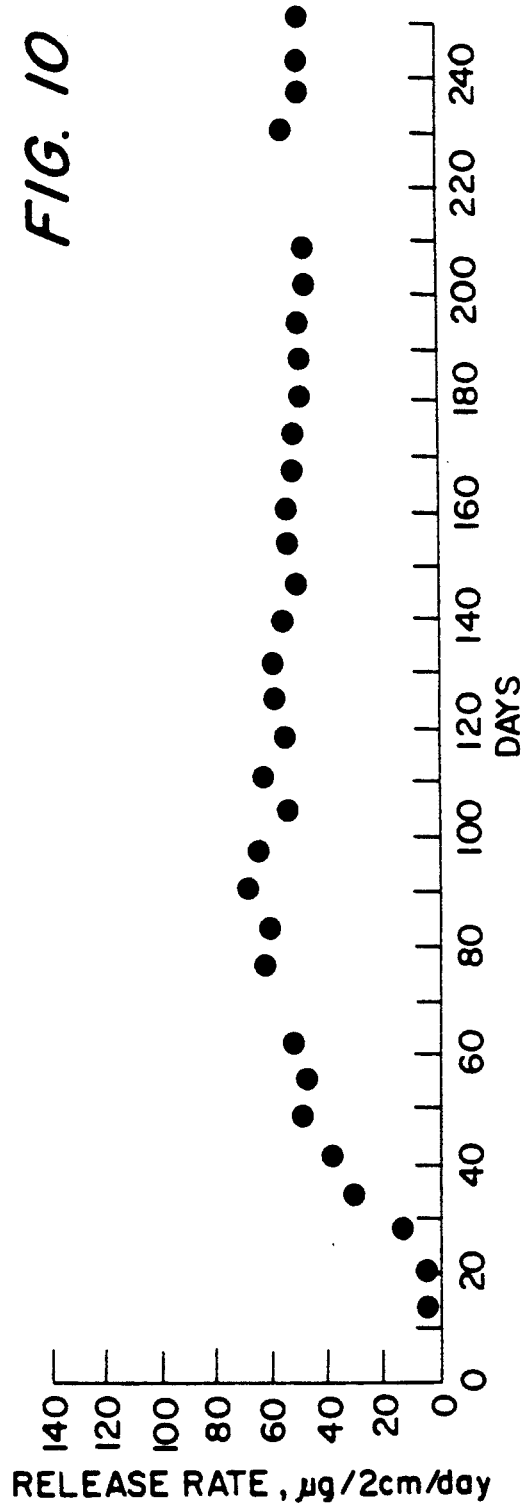

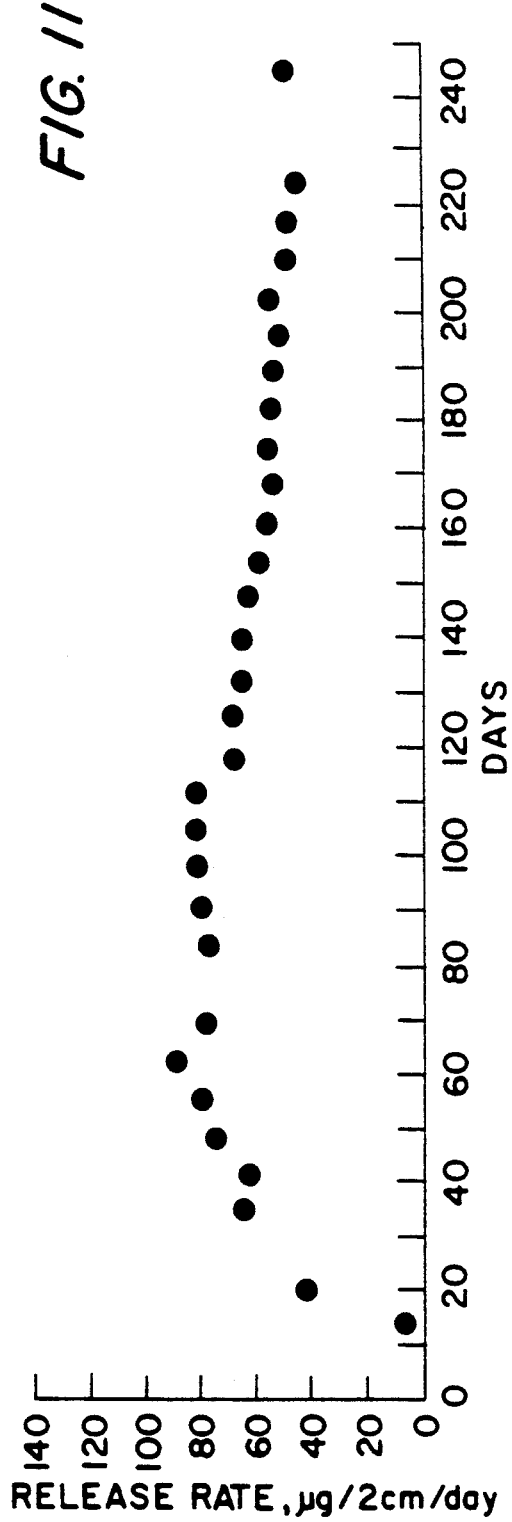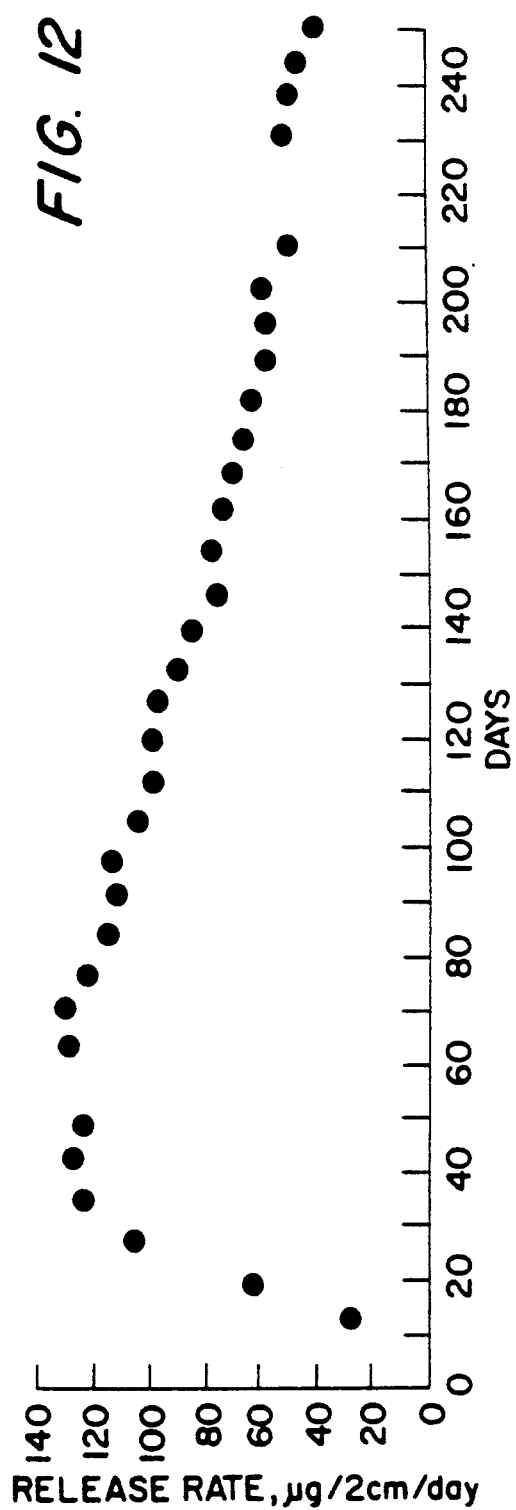

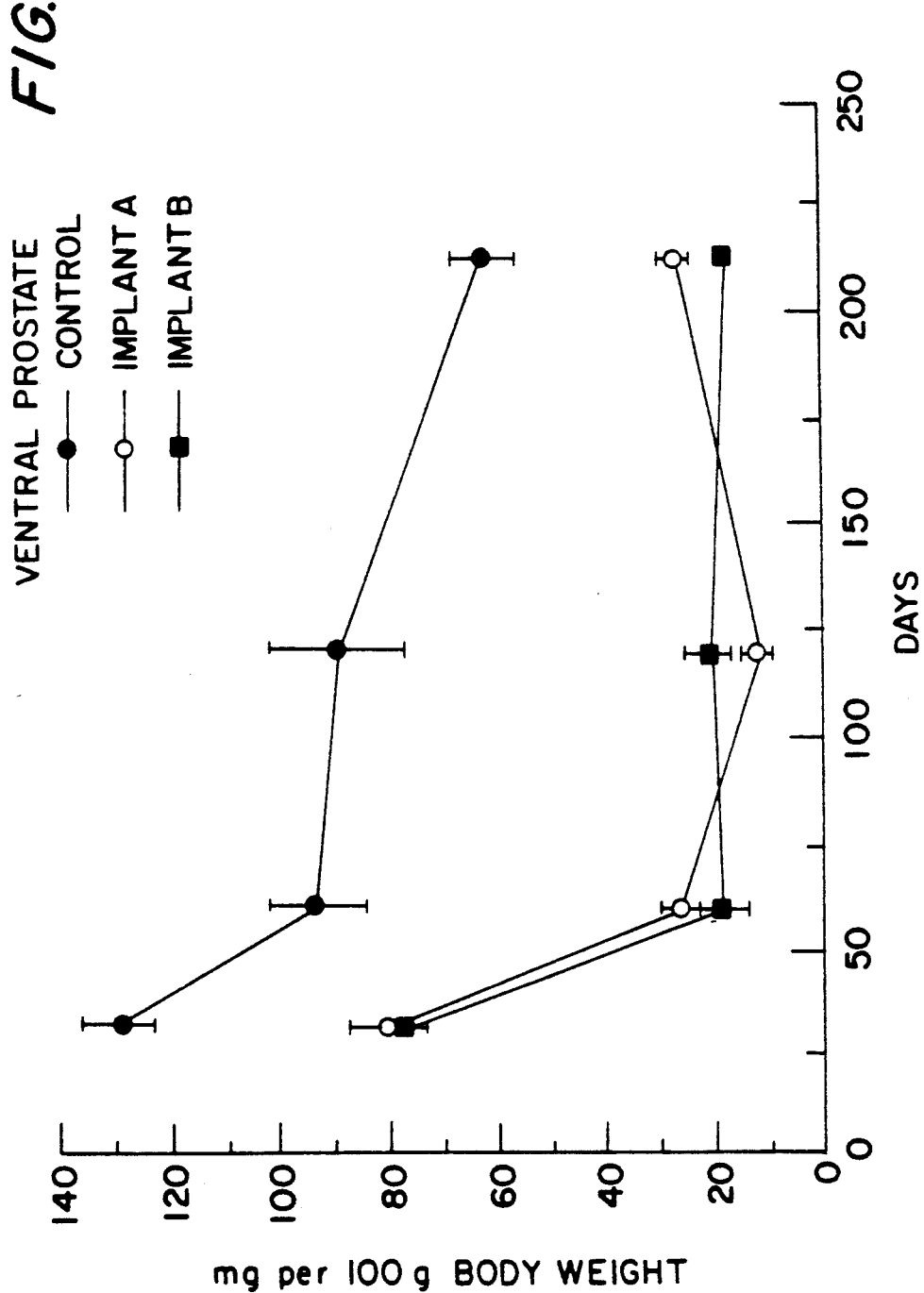

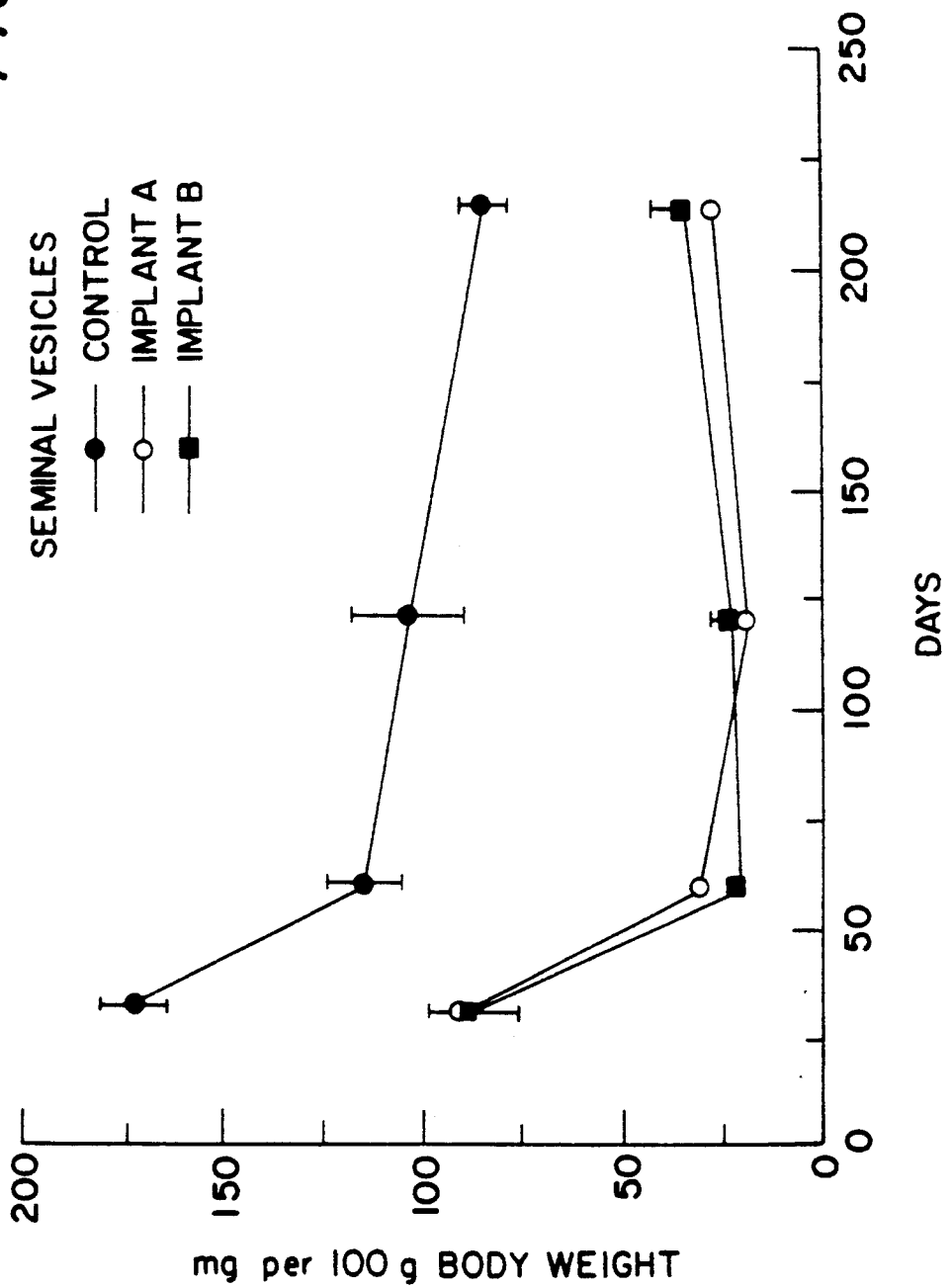

MANUFACTURE OF WATER-SWELLABLE HYDROPHILIC ARTICLES AND DRUG DELIVERY DEVICES

This is a continuation of prior application Ser. No. 07/589,957, filed on Sep. 28, 1990, now abandoned.

DESCRIPTION

The present invention relates to a hydrophilic article and to a method for centrifugally casting such article. In one aspect, the invention relates to a drug delivery device comprised of inert, biocompatible, non-toxic, non-biodegradable, water-swellable, water-insoluble, hydrophilic material and its hydrated form, and a drug capable of being released therefrom in a sustained and/or controllable manner to a delivery environment.

BACKGROUND OF THE INVENTION

The sustained release of active agents from drug delivery devices, for example, in the form of an ocular insert, tablet, transdermal patch, or implantable device is well known. In the administration of certain pharmaceuticals, long-term drug delivery has been shown to be effective in that constant serum levels are obtained and patient compliance is improved. Delaying the release of the active agent is also desirable in that an immediate release upon placement in the delivery environment can result in unacceptably high initial concentrations of a drug at the sites of implantation.

The examination of synthetic hydrogels for potential biomedical applications (including potential use in certain drug delivery devices) has given rise to various theories regarding mechanisms of diffusion. Lee, Jhon and Andrade have proposed that there are three classes of water in hydrogels, using poly(2-hydroxyethyl methacrylate), oftentimes abbreviated as polyHEMA, as their model [Nature of Water in Sythetic Hydrogels, J. Colloid & Interface Sci., 51 (2): 225-231 (1975)]. The first 20% of hydrogel water content, called "Z water", was said to be bound to the polymer matrix. The next 10-12% of water content, called interfacial or "Y water", is partially affected by the polymer matrix. Any additional water imbibed by the gel is relatively unaffected by the polymer matrix; it is called bulk or "X water".

The Lee, et al. model was expanded upon by Kim, Cardinal, Wisniewski and Zentner [Solute Permeation Through Hydrogel Membranes: Hydrophilic vs. Hydrophobic Solutes, ACS Symposium Series (Water in Polymers), 127 (20): 347-359 (1980)]. They concluded that the diffusion coefficients for hydrophilic solutes through hydrogel membranes depends on molecular size and water content; permeation in pure polyHEMA and in polyHEMA crosslinked with a low mole percent of ethylene glycol dimethacrylate was via the pore mechanism, i.e., through the bulk-type water. Hydrophobic solutes were said to diffuse via both pore and partition mechanisms, i.e., respectively through the bulk-type water, and through the interfacial-type and bound-type water.

Wood, Attwood and Collett have described a model for diffusion of the small hydrophobic molecule salicylic acid (the solute) in hydrogels [The Influence of Gel Formulation on the Diffusion of Salicylic Acid in PolyHEMA Hydrogels, J. Pharm. Pharmacol., 34: 1–4 (1982)]. Radioactively labeled salicylic acid was added to a HEMA monomer solution and polymerized in situ. The water contents of the resulting gels were measured. Diffusion was measured by quantifying migration of the solute to a gel placed in contact with the sample gels. It was concluded that diffusion occurred primarily through the polymer's pores via the hydrating liquid at higher levels of hydration (more than 31%). At hydration levels below 31%, diffusion was said to occur by dissolution of the solute within the polymer segments; crosslinker concentration did not have any significant effect on diffusion. This was correlated to a change in pore size proportional with percent hydration. For another treatment of the interaction of pore size and diffusion, see Wisniewski and Kim [J. Membrane Sci., 6: 299-308 (1980)].

Microporous membranes (some including hydrogels) have been used as rate-limiting barriers for such devices, including implants, ocular inserts, coated intrauterine devices and the like, for example, as described in U.S. Pat. Nos. 3,416,530, 3,618,604, and 3,828,777 to Ness; U.S. Pat. No. 3,551,556 to Kliment, et al; U.S. Pat. No. 4,548,990 to Mueller, et al.

In U.S. Pat. Nos. 3,993,072, 3,948,254, and 3,854,380 to Zaffaroni, drug delivery systems are disclosed including a solid inner matrix containing a drug and surrounded by a wall formed of a polymeric membrane (the '072 and '254 patents call for a microporous membrane, the pores of which contain a drug-release-rate-controlling medium).

Some sustained release devices have been described for the delivery of hydrophilic macromolecules, such as polypeptides. For example, European Patent Application Publication No. 0,092,918 to Churchill, et al. entitled "Continuous Release Formulations" describes the continuous release of, e.g., luteinizing hormone-releasing hormone, growth hormones and growth hormone releasing factor, from a hydrophobic/hydrophilic non-crosslinked copolymer in which the hydrophobic component is biodegradable and the hydrophilic component may or may not be biodegradable. The composition is described as being capable of absorbing water to form a hydrogel when placed in an aqueous, physiological-type environment.

In European Patent Application Publication No. 0246653, publication date Nov. 25, 1987, in the names of Sanders and Domb there is disclosed a drug delivery device comprising a pharmaceutically acceptable carrier, macromolecules of at least 1,000 molecular weight mixed with said carrier, and a partially-hydrated, non-biodegradable, hydrogel rate-limiting membrane, such as crosslinked poly(2-hydroxyethyl methacrylate), which surrounds or envelops the drug and carrier. The examples disclose a cylindrical reservoir-type delivery device formed by polymerizing a mixture of 2-hydroxyethyl methacrylate (HENU) and ethylene glycol dimethaciylate (EGDMA) in a cylindrical mold, with or without a core. When a mold without a core is used, a core is drilled into the cylindrical polymer matrix. The reservoir is then filled with an amount of suspended drug sufficient to carry out the treatment regimen. A fresh mixture of HESM and EGDMA is added to the top of the reservoir and polymerized to effect a seal.

The patent applicants further disclose the preparation of polymer rods of HEMA/EGDMA using small glass vials (about 3 cm×0.6 cm) as the polymerization vessel. After completion of the polymerization reaction, polymer rods (2.5 cm in length and 6.0 mm in diameter) are recovered by breaking the glass vials and they are thereafter placed in a desiccator maintained at a humidity of 23 percent for 6 hours. To fabricate a core (reservoir) in the rods, the patent applicants disclose the following:

"The rods were removed from the desiccator and carefully drilled to form a reservoir having a diameter of 4.0 mm, proceeding with the drill in about 0.5 cm steps, followed by removal of the drill bit from the rod for cooling (by immersion in water or by application of a cold air) before commencing the next 0.5 cm step. Drilling is continued until a reservoir of sufficient volume is formed, in no event drilling closer to the end of the rod than the thickness of the reservoir (i.e., 2.0 mm). It was observed that having the rods in a partially hydrated state was of significant benefit for the drilling operation. Fully hydrated rods were found to be too flexible and soft. Dry rods were found to be too stiff and easy to crack during drilling."

The fabrication of partially hydrated rods, as proposed above, for use in a drug delivery device is quite labor intensive, tedious, and expensive. The drilling procedure, effected in several steps on the small partially hydrated rods, results in a core (the reservoir) whose surface suffers from a lack of uniformity and desired smoothness. Additionally, the thickness between the core surface and the outer surface of the rod would lack uniformity and cause an irregular release rate of the macromolecules. The device thus suffers from poor geometry and is relatively bulky.

Davidson, Domb, Sanders, and McRae disclose that hydrogel membranes of polyHEMA and HEMA/methyl methacrylate copolymer can be used for controlled delivery of analogs of LHRH. Cylindrical implant devices of crosslinked poly(2-hydroxyethyl methacrylate) containing excess LHRH analog (RS-49947) dispersed in silicone oil were implanted in several beagles for one year. Several of the devices, because of the low mechanical strength of the hydrogel polymer, did not remain intact for the whole year; however, of those devices remaining intact estrus was suppressed in the female beagles [Hydrogels for Controlled Release of Peptides, Proceed. Intern. Symp. Cont. Rel. Bioact. Mater., 15, (1988), Controlled Release Society, Inc.].

U.S. Pat. Nos. 4,517,138 and 4,517,139 to Rawlings et al disclose a method for spin casting contact lenses by employing a polymerization tube which is adapted to receive and accommodate a plurality of vertically arranged circular molds in interference fitting relationship. Each mold contains lens-forming material in the mold cavity. The polymerization tube with its interior filled with stacked molds is rotated about its longitudinal axis, maintained perpendicular to the ground, under polymerization conditions. Rotation of the tube will cause the stacked molds to rotate at the same speed while maintaining the concentricity of the molds to the spinning axis of the tube to produce the lenses.

SUMMARY OF THE INVENTION

Shaped articles, formed of xerogel or hydrogel, of predetermined dimensions, useful as a rate-limiting barrier of an active compound, e.g., a drug, are prepared via a centrifugal casting method which comprises:

a. introducing into the open end of a polymerization column a predetermined amount of polymerizable, liquid material;

b. rotating said polymerization column about its longitudinal axis maintained substantially parallel to the ground at a speed sufficient to cause radially outward displacement of said polymerizable liquid material to assume a predetermined hollow cylindrical liquid configuration within said column;

c. maintaining the polymerization column under polymerization conditions to convert said polymerizable material of predetermined liquid configuration into a predetermined solid hollow cylindrical configuration; and d. recovering a solid, hollow cylindrically-shaped article formed of water-swellable, water-insoluble polymer having a closed end and an open end, a cylindrical core or reservoir, and smooth internal and external cylindrical surfaces of substantial uniform thickness between the said surfaces.

Another aspect of the invention relates to a method of preparing a uniform, cylindrically-shaped polymeric cartridge with a concentric core, said cartridge characterized by a water-insoluble, water swellable polymeric matrix and a pore-forming agent uniformly or homogeneously distributed therein which comprises:

a. introducing a homogeneous or uniform mixture of predetermined amounts of polymerizable liquid material and a water-soluble, pore-forming agent into a polymerization column, e.g., an elongated tube;

b. rotating said polymerization column about its longitudinal axis maintained substantially parallel to the ground at a speed sufficient to cause radially outward displacement of said mixture to assume a predetermined liquid cartridge configuration within said column;

c. maintaining the polymerization column under polymerization conditions to convert said mixture of predetermined liquid configuration into a predetermined solid cartridge; and d. recovering said cartridge characterized by substantial uniformity of thickness between its outer and inner cylindrical surfaces ($D_o - D_i$ = Constant) and having a water-soluble pore-forming agent uniformly or homogeneously distributed throughout the cartridge.

Another aspect, the invention relates to a method for the preparation of a delivery device for the delayed/sustained release of an active agent therefrom e.g., a drug, which comprises:

a. introducing active agent and, optionally, a pharmaceutically acceptable carrier, into the core (reservoir) of the aforesaid cylindrically shaped body in an amount sufficient for extended sustained release of said active agent into a delivery environment;

b. further introducing polymerizable liquid material into the said core in an amount sufficient to fill the core to the top of the cylindrical body, said polymerizable liquid material in its polymerized state having an equilibrium water content value which exceeds the equilibrium water content value of the cylindrical body; and c. polymerizing said polymerizable material to effectively seal the core opening with a plug (layer) of water-swellable, water-insoluble polymer.

In another aspect, the invention relates to a drug delivery device per se for the delayed/sustained release of an active agent to a delivery environment. The device comprises a hydrophilic cartridge of xerogel or hydrogel with a core of smooth, unscored cylindrical surface; hydrophilic sealing means to seal the open end of the cartridge thereby defining an enclosed core; an active agent, and optionally, a pharmaceutically acceptable carrier, contained in the core in an amount sufficient to be continually released over an extended period of time into a delivery environment; the said cartridge being characterized by water-swellability and water-insolubility; and the said hydrophilic sealing means being characterized by water-swellability, water-insolubility, and an equilibrium water content value which exceeds that of said cartridge.

Another aspect of the invention relates to a kit for the implantation, desirably subcutaneously, of the aforesaid drug delivery device in an animal. The delivery device is amenable to long term implantation since degradation products are not dispersed throughout the body and the hydroactive compound is released in a relatively controlled manner into the delivery environment. The device being non-biodegradable remains intact and is retrievable; radioactive material can be used in the fabrication of the device or contained in the reservoir to facilitate location. In small rod-like form with a concentric cylindrical core, the drug delivery device can be packaged as part of a sterilized kit, with a suitable hypodermic syringe-like instrument or a trocar tailored for the intended use.

A further aspect of the invention relates to a method for introducing a cylindrically-shaped drug delivery device into an animal body by circular perforation to provide sustained release of a drug into said body which includes selecting an area of the body to be treated; implanting into the living tissues of the body the drug delivery device through a cannula of, for example, a trocar-like or hypodermic needle/syringe-like instrument; said delivery device comprised of a drug and, optionally, a pharmaceutically acceptable carrier sealed in a reservoir of a hydrophilic, rate-limiting cylindrically-shaped plastic article; and removing said cannula from said body.

OBJECTS OF THE INVENTIONS

Accordingly, one or more objects of the invention will be achieved by the practice of the inventions herein described.

It is an object of the invention to provide a method for centrifugally casting a cylindrical plastic article of good mechanical properties, said article being characterized by a cylindrical core, smooth unscored cylindrical surfaces, and uniformity of thickness between said surfaces.

It is another object of the invention to provide a drug delivery device for the delayed/sustained release of an active agent contained therein, said device characterized by improved surface characteristics and resistance to mineralization in vivo.

It is a further object of the invention to provide a drug delivery device comprised of an active compound and optionally a pharmaceutically acceptable carrier contained in the reservoir of a hollow cylindrical article which is sealed, at one end thereof, with unique leak proof closure means.

It is still another object of the invention to provide a disposable, sterilized kit comprising a hydrated drug delivery device and injection means for the subcutaneous implantation of said device in an animal body.

Another object of the invention is to provide reproducible hydrophilic cartridges, of predetermined precise dimensions useful in the fabrication of drug delivery devices, by a simple, time-saving, and cost effective centrifugal casting method which comprises reacting unique polymerizable systems to form predetermined shaped hydrophilic cartridges in situ, followed by post-curing and annealing steps, to yield relatively stress-free cartridges of good mechanical integrity.

It is another object of the invention to provide for the fabrication of water-swellable, water-insoluble cartridges of various predetermined equilibrium water content useful in drug delivery devices by a method which comprises polymerizing a monomeric mixture containing 2-hydroxyethyl methacrylate (a hydrophilic monomer) and a predetermined amount of a second hydrophilic monomer, e.g., hydroxypropyl methacrylate, to form a substantially homogeneous polymer (in terms of polarity), essentially void of non-polar, hydrophobic regions, and of improved mechanical strength and elasticity.

A still further object of the invention is to provide a hydrophilic cartridge useful in drug delivery implants for the delayed/sustained release of a pharmaceutically acceptable amount of a drug to a body environment.

A yet further object of the invention is to provide thin, uniform, hydrophilic cartridges comprised of water-soluble, pore-forming agent(s) homogeneously distributed therein, said cartridges being useful in drug delivery implants, said agent(s) being removed by dissolving or leaching in an aqueous medium thus imparting a porous structure to said cartridge.

These and other objects will become apparent to those skilled in the art from a consideration of the specification.

BRIEF DESCRIPTION OF THE DRAWINGS

FIG. 1 is a side elevation view, partly in cross-section, of a polymerization column (tube) open at one end and closed with a Delrin ® plug at the other end and containing polymerizable material within its interior prior to mounting and rotating the column horizontally on a suitable machine.

FIG. 1a is a blown-up, side elevation view, in cross-section, of spindle plug assembly 20.

FIG. 2 is a partial side elevation view of a polymerization column horizontally mounted to a suitable lathe and containing a spin cast molded hydrophilic cartridge of predetermined dimensions within its core.

FIG. 3 is an enlarged side elevation, partly in cross-section, of a drug delivery device comprised of a drug and a pharmaceutically acceptable carrier contained in a cylindrically-shaped hydrophilic body.

In FIGS. 7–13, the release rates of a luteninizing hormone-releasing hormone, averaged over a seven day period, were normalized to an implant of 20 mm, standard reservoir length.

FIG. 7 is a graph showing in vitro release profile vs. time in days for LHRH-13 ($\mu$g/2 cm/day) through a cylindrically-shaped implant of crosslinked hydrophilic polyHPMA polymer at equilibrium water content. The scale on the ordinate axis (y-axis) was expanded four times to accommodate the extremely low release rate of LHRH-13. LHRH-13 is a luteinizing hormone releasing hormone polypeptide identified as [DHis(imBzl)$^6$ProN-HEt]-GnRH].

FIG. 8 is a graph showing in vitro release rate profile vs. time in days for LHRH-13 ($\mu$g/2 cm/day) through a cylindrically-shaped implant of crosslinked hydrophilic 35% HEMA/64.5 HPMA polymer at equilibrium water content.

FIG. 9 is a graph showing in vitro release rate profile vs. time in days for LHRH-13 ($\mu$g/2 cm/day) through a cylindrically-shaped implant of crosslinked hydrophilic 40% HEMA/59.5% HPMA polymer at equilibrium water content.

FIG. 10 is a graph showing in vitro release rate profile vs. time in days for LHRH-13 ($\mu$g/2 cm/day) through a cylindrically-shaped implant of crosslinked hydrophilic 50% HENW/49.5% HPMA polymer at equilibrium water content.

FIG. 11 is a graph showing in vitro release rate profile vs. time in days for LHRH-13 ($\mu$g/2 cm/day) through a cylindrically-shaped implant of crosslinked hydrophilic 60% HEMA/39.5% HPMA polymer at equilibrium water content.

FIG. 12 is a graph showing in vitro release rate profile vs. time in days for LHRH-13 ($\mu$g/2 cm/day) through a cylindrically-shaped implant of crosslinked hydrophilic 70% HEMA/29.5% HPMA polymer at equilibrium water content.

FIG. 13 is a graph showing in vitro release rate profile vs. time in days for LHRH-40 ($\mu$g/2 cm/day) through a cylindrically-shaped implant of crosslinked hydrophilic polyHEMA polymer at equilibrium water content.

FIGS. 15 through 18 are graphs showing the in vivo release of LHRH-13 in rats from cylindrically-shaped delivery devices fabricated of crosslinked HEMA/HPMA polymers and the effect on suppression of the testes and accessory sex glands. The hydrogel polymer of Implant A is 50% HEMA/49.5% HPMA/0.5% TMPTMA polymer and the hydrogel polymer of Implant B is 40% HEMA/59.5% HPMA/0.5% TMPTMA polymer.

DETAILED DESCRIPTION OF THE INVENTIONS

Figure 4:
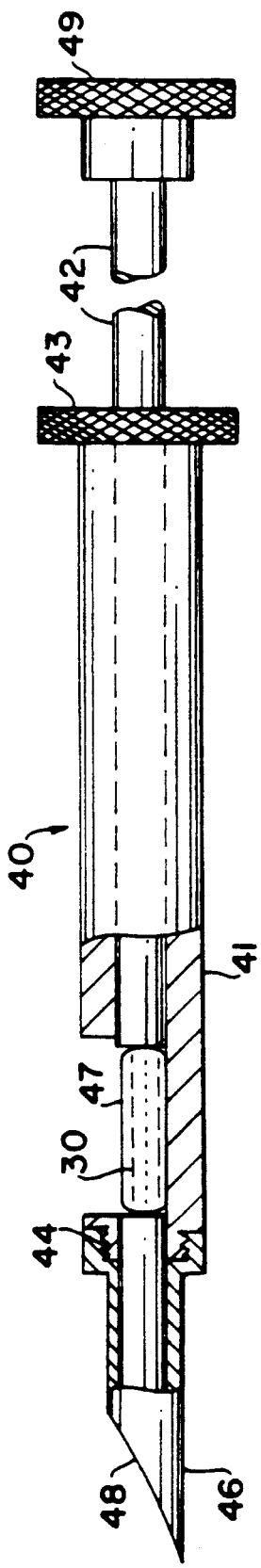
FIG. 4 is a side elevation view partly in cross section of a metal trocar containing a cylindrically-shaped drug delivery device for deposition to a preselected site of an animal.

The novel method of centrifugally casting a novel hydrophilic cylindrically-shaped solid article with a concentric cylindrical core or reservoir comprises: (a) introducing liquid polymerizable material into a polymerization column, e.g., a tube, adapted for rotation about its longitudinal axis, one extremity of said column being closed, the other extremity being open-ended; (b) rotating said column about its longitudinal axis maintained parallel to the ground or substantially so; (c) said rotation being effected at a speed sufficient to cause radially outward displacement of said liquid polymerizable material to assume a predetermined liquid cylindrical configuration having a core; (d) maintaining said column under polymerization conditions to convert said liquid polymerizable material of predetermined liquid configuration into a predetermined cylindrically-shaped solid article having a concentric cylindrical core; and (e) recovering said solid article.

The polymerization column can be a suitable hollow tube fabricated of various materials such as plastics, e.g., polyethylene, polypropylene, and polystyrene; glass; and the like. Cross-sectional areas of the interior of the column are circular in shape and of equal diameter. In preferred embodiments, the column is fabricated from a material that will not significantly impede the transmission of radiation into the polymerization zone of the column. Glass, such as Pyrex ®, is a preferred material for the polymerization column when using radiation with/without initiation(s) and/or other catalyst(s).

Liquid polymerizable material useful in the manufacture of the novel hydrophilic cylindrically-shaped articles include a wide variety of polymerizable hydrophilic, ethylenically unsaturated compounds, in particular, hydrophilic monomers such as the monoester of an acrylic acid or methacrylic acid with a polyhydroxy compound having an esterifiable hydroxyl group and at least one additional hydroxyl group such as the monoalkylene and polyalkylene polyols of methacrylic acid and acrylic acid, e.g., 2-hydroxyethyl methacrylate and acrylate, diethylene glycol methacrylate and acrylate, propylene glycol methacrylate and acrylate, dipropylene glycol methacrylate and acrylate, glycidyl methacrylate and acrylate, glyceryl methacrylate and acrylate, and the like; the N-alkyl and N,N-dialkyl substituted acrylamides and methacrylamides such as N-methylmethacrylamide, N,N-dimethylmethacrylamide, and the like; N-vinylpyrrolidone; the alkyl-substituted N-vinylpyrrolidones, e.g., methyl substituted N-vinylpyrrolidone; N-vinylcaprolactam; the alkyl-substituted N-vinylcaprolactam, e.g., N-vinyl-2-methylcaprolactam, N-vinyl-3,5-dimethylcaprolactam, and the like.

In the practice of the novel process for preparing the novel hydrophilic cartridges, the polymerizable hydrophilic material can also include minor amounts of a polymerizable hydrophobic monomer(s), i.e., upwards to about 30 weight percent and higher, based on the total polymerizable monomers, thereby varying the equilibrium water content value of the resulting water-swellable polymeric cartridge. It was observed that a polymerization mixture containing increasing amounts of the hydrophobic monomer, e.g., methyl methacrylate, resulted in heterogeneous hydrophilic polymers of decreasing equilibrium water content. However, though these polymers are disclosed in the art as useful in drug delivery devices, they contain alternating hydrophobic and hydrophilic regions and are non-homogeneous in terms of polarity. A non-polar crosslinking agent, e.g., EGDMA, will tend to concentrate during the polymerization reaction in the non-polar hydrophobic regions of the polymer (as it forms) thereby causing a crosslinking density gradient in the polymer. Such polymers, being heterogeneous in their structure, are characterized by over-crosslinking in the hydrophobic segments and by under-crosslinking in the hydrophilic segments. Over-crosslinking and under-crosslinking can impart weak and fragile properties to such polymers.

Highly preferred aspects of the inventions, therefore, include the novel homogeneous hydrophilic cartridges whose polymer structure is formed via the polymerization of hydrophilic material, especially mixtures comprising at least two polymerizable hydrophilic monomers, and in particular, mixtures such as 2-hydroxyethyl methacrylate plus hydroxypropyl methacrylate or 2-hydroxyethyl methacrylate plus N-methylacrylaniide; and the novel drug delivery devices which utilize the preferred polymer cartridges in their delivery system.

Figure 6:
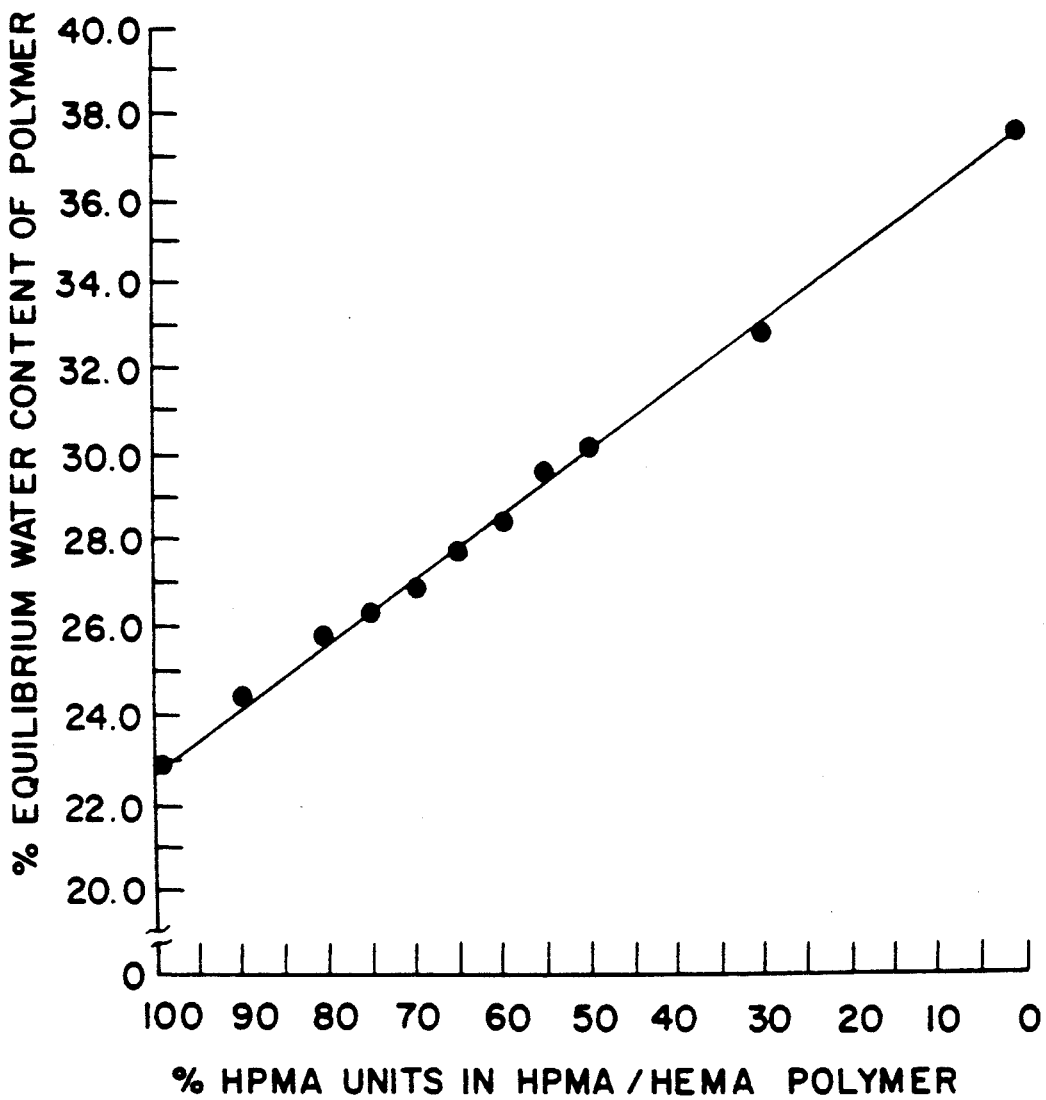
FIG. 6 is a graph showing the linear relationship between the equilibrium water content vs. the weight percent content of 3-hydroxypropyl methacrylate ("HPNW") units in crosslinked HEMA/HPMA polymers at their maximum state of hydration.

In these preferred aspects, tailor-made hydrophilic cartridges of predictable hydrophilicity, e.g., equilibrium water content, can be prepared by polymerizing a mixture comprising, for example, varying amounts of two major hydrophilic monomers as illustrated in FIG. 6. The resulting tailor-made cartridges are homogeneous polymers, not heterogeneous polymers. When hydrophobic segments are present in the polymer, the interfacial free energy increases thus enhancing protein adsorption and mineralization after implantation in an animal. Hydrogels of polyHEMA were measured to have interfacial free energy close to zero. According to the interfacial free energy interpretation, hydrogels of strictly hydrophilic components would strongly appear to be biocompatible with body tissue. PolyHEMA is a homogeneous, hydrophilic "homopolymer" (disregarding the relatively small quantities of polymerized crosslinking agent therein) of relatively fixed characteristics or values. Techniques of altering the "homopolymer" to impart to it additional characteristics or properties are difficult, time-consuming, and oftentimes result in erratic property behavior. On the other hand, mixtures of HEMA with varying quantities of other polymerizable hydrophilic comonomer(s) can be polymerized to give predictable homogeneous hydrophilic copolymers having (predetermined) tailor-made properties.

The polymerizable hydrophobic comonomers are substantially water-insoluble compounds lacking hydrophilic groups or other groups that would increase the equilibrium water content value of the resulting hydrophilic heterogeneous polymer. As indicated previously, the incorporation of increasing amounts of a hydrophobic comonomer(s) to a polymerizable mixture containing polymerizable hydrophilic monomer(s), it was observed, gave heterogeneous hydrophilic polymers of corresponding lower equilibrium water content values. Illustrative polymerizable hydrophobic comonomers include the alkyl 2-alkenoates, the alkoxyalkyl 2-alkenoates, and the vinyl esters, such as alkyl acrylate, alkyl methacrylate, alkoxyalkyl methacrylate, alkoxyalkyl acrylate, poly(alkoxy)alkyl methacrylate, vinyl alkanoate, and the like. Specific examples are methyl acrylate, methyl methacrylate, ethyl acrylate, ethyl methacrylate, propyl methacrylate, butyl acrylate, butyl methacrylate, methoxymethyl acrylate and methacrylate, ethoxymethyl acrylate and methacrylate and methoxyethyl methacrylate, vinyl acetate, and vinyl propionate.

In one embodiment, a pore-forming material can be included with the polymerizable hydrophilic material. The pore-formers can be liquid or solid and are uniformly distributed or dispersed in the reaction medium. The pore-formers can be organic or inorganic and can be extracted from the resulting hydrophilic cartridge, by extraction or leaching, without any chemical change in the hydrophilic polymer. The pore-formers, in particulate form, can range in size from less than 0. 1 micron to several microns depending on the porosity desired in the hydrophilic polymer. Illustrative pore-formers include sodium chloride, potassium phosphate, calcium nitrate, mono- and polysaccharides, and the like.

Useful crosslinking agents which can be included in the polymerizable reaction medium include, for example, the polyethylenically unsaturated compounds having at least two polymerizable ethylenic sites, such as the di-, tri- and tetra-ethylenically unsaturated compounds, in particular, the tri-unsaturated crosslinking agents with/without the diunsaturated crosslinking compounds, for example, divinylbenzene, ethylene glycol dimethacrylate and diacrylate, propylene glycol dimethacrylate and diacrylate; and the di-, tri- and tetraacrylate or methacrylate esters of the following polyols: triethanolamine, glycerol, pentaerythritol, 1,1,1-trimethylolpropane; and others.

The polymerization reaction can be carried out in bulk or with an inert solvent. Suitable solvents include water; organic solvents such as water-soluble lower aliphatic monohydric alcohols as well as polyhydric alcohols, e.g., glycol, glycerine, dioxane, etc.; and mixtures thereof.

Compounds useful in the catalysis of the polymerizable ethylenically unsaturated compounds include the free-radical compounds and/or initiators of the type commonly used in vinyl polymerization such as the organic peroxides, percarbonates, hydrogen peroxides, and alkali metal sulfates. Illustrative examples include cumene hydroperoxide, t-butyl hydroperoxide, benzoyl peroxide, bis(4-t-butylcyclohexyl) peroxydicarbonate, hydrogen peroxide, 2,4-dichlorobenzoyl peroxide, acetyl peroxide, di-n-propyl peroxydicarbonate, di-t-butyl peroxide, di-sec-butyl peroxydicarbonate, ammonium sulfate, potassium sulfate, and sodium sulfate. A preferred catalyst is one which is effective at moderately low temperature such as at about 20°-80° C., such as tert-butyl peroctoate, benzoyl peroxide, and di(secbutyl) peroxydicarbonate.

A conventional redox polymerization catalyst can also be employed. The advantage of redox initiation is that the reaction occurs at reasonable rates at low temperatures, e.g., 0° C. to 50° C. A large number of reductant-oxidant pairs producing free radicals is known in the art. Examples include sodium bisulfate and ammonium persulfate, sodium thiosulfate and potassium persulfate, and the like.

Preferably, polymerization of the ethylenic compounds can be effected using radiation, e.g., U.V., X-Ray, gamma radiation, microwave, or other well-know forms of radiation. A preferred catalyst for U.V. cure is benzoin methyl ether.

Catalysts and/or initiators and/or radiation are employed in a catalytically effective amount to optimize the polymerization reaction.

In additional aspects, the hydrophilic cartridges, suitably stored in a dry environment, are utilized in the fabrication of the drug delivery device. A predetermined amount of an active compound per se or as an admixture with an inert, non-toxic material or as a suspension in a non-toxic medium, e.g., medical grade silicone oil, is introduced into the cartridge to partially fill the core. The top of the active compound is preferably covered with a layer of an inert material, e.g., teflon tape. The void in the core above the covering is thereafter sealed to prevent leakage into or out of the cartridge. Preferably the closure is formed by filling the void with polymerizable material and effecting a polymerization reaction to form a plug of hydrophilic polymer which seals the opening of the cartridge. The hydrophilic polymer plug, upon maximum hydration, will have an equilibrium water content value exceeding the equilibrium water content value of the hydrophilic cartridge. Using polymerizable material comprising ethylenically unsaturated monomer(s) and desirably crosslinking agent(s), a polymer plug grafted to the inner surface of the cartridge can be obtained.

In one embodiment, a hermetical closure of the cartridge can be accomplished in the following illustrative manner. The internal surface area of the core above the active compound or teflon tape, if used, is cleaned and slightly increased by careful reaming with an appropriate reamer. The reamed surface area is then cleaned with a sufficient amount of a mono- or polyhydric alcohol, e.g., $C_1-C_4$ alcohol such as ethanol, whereby causing a slight swelling of the surface. This technique promotes the penetration of the polymerizable hydrophilic material into the treated surface. Using a fine needle-syringe, a small amount of polymerizable material (with initiator) is injected into the cartridge until the core is filled to the top. Preferably the polymerizable material will be of similar composition but of higher hydrophilicity than that employed in the fabrication of the cartridge. The cartridge filled with active compound and polymerizable material, with its longitudinal axis perpendicular to the ground, is rotated on a suitable machine such as a lathe at a relatively low speed, e.g., 100 to 200 rpm, at ambient room temperature while exposed to U.V. light for several minutes, e.g., 5-10 minutes. In the event the active compound, e.g., drug, is sensitive to U.V. light, a suitable shield such as aluminum foil can be used to shield the active compound from the U.V. light. The postcure step is effected at a temperature that is not detrimental to the drug. There is obtained a plug of polymer hermetically sealing the core opening. As will be apparent from the operative examples herein, the seal between the plug and the internal surface of the cartridge is stronger than the cartridge wall.

The inventions will become more apparent from the present disclosure when considered together with the accompanying drawings which are exemplary of aspects and embodiments thereof.

Referring to FIG. 1, there is disclosed a polymerization column 10 having a concentric cylindrical core 11 of smooth, unscored surface and which contains a predetermined amount of polymerizable hydrophilic liquid mixture 12 containing, for example, hydrophilic monomer, crosslinking agent, catalyst, and initiator. Removable Delrin ® plug 13 comprises head means 14 and stem means 16. Stem means 16, received in friction fit within core 11, seals one opening column 10. Head means 14 is adapted to be received in hollow portion 17 and locked in collet chuck 18. A suitable machine such as a lathe with a motor of variable controlled speed (not shown) is connected to collet chuck 18 to provide for horizontal rotation of the column about its longitudinal axis A—A'. Spindle plug assembly 20 comprises outer plug 21, bearing shield 22, and inner plug 23 and is multifunctional. Inner plug 23 is snugly received within the inner race of ball bearing 24 which is also retained in proper relationship by securing means not shown. Outer plug 21 is adapted to be received in friction fit at opening 19 of the column. Bearing shield 22 functions as a protective shield for ball bearing 24. The outer race of ball bearing 24 is locked in chuck collet 26 of a lathe slide bar (not shown) adapted for left to right positioning and for insertion and withdrawal of outer plug 21 at opening 19.

The air space in the column defined by polymerization mixture 12 and opening 19 is gently purged with nitrogen using a syringe needle not shown. After purging, column 10 is sealed by inserting outer plug 21 into opening 19. The column, with its longitudinal axis parallel to the ground, is rotated at a speed, e.g., 2,150 rpm, and ambient room temperature (approximately 22° C.), sufficient to cause radially outward displacement of the polymerizable liquid to its internal cylindrical surface thereby forming, upon stabilizing, a predetermined hollow cylinder of said liquid (a predetermined liquid cartridge shape). Ultra-violet light, not shown, is then directed at the shaped polymerizable liquid until it is polymerized to the predetermined cylindrically-shaped article with a concentric core.

Referring to FIG. 2, the internal surface of polymerization column 10 is contiguous to the external surface of a solid polymeric cartridge 31 which has an outer cylindrical surface and an inner smooth, unscored cylindrical surface 32 defining a substantially uniform wall thickness, i.e., $D_o - D_i = K$ wherein $D_o$ is the outer diameter of the cartridge, wherein $D_i$ is the inner diameter of the cartridge, and wherein K is a constant. The internal surface at base 33 is slightly oval in shape. Excess base 33 can be removed by cutting and its external surface polished to an oval-like cylindrical design.

FIG. 3 shows one form of a drug delivery device 30 of the invention. Cartridge 31 is shown with an oval-like base 33 (after trimming and polishing) packed with drug 34 in its core. The external and internal cylindrical surfaces of cartridge 30 are smooth and unscored. Teflon cover 36 separates drug 34 from hydrophilic plug 37, formed in situ from liquid material and polymerized to a solid hydrophilic plug 37. The equilibrium water content of plug 37 and thus its swellability are greater than the equilibrium water content of cartridge 31 therefore forming a hermetical seal upon hydration. The outer surface 38 of plug 37 including a portion of the contiguous cartridge wall 39 has been oval-shaped by trimming and polishing.

Referring to FIG. 4, one form for the implantation of a novel hydrated drug delivery device in an animal is shown. Trocar 40, a needle-syringe type instrument desirably fabricated of metal for injecting drug delivery device 30 into an animal comprises circular barrel 41 with a core for slidably receiving rod 42, retaining plate 43, and a threaded end 44 for accepting (disposable) threadable needle number 46. Drug delivery device 30 in a hydrated state rests in circular chamber 47. Needle member 46 having a hollow needle opening 48 is threaded at the end opposite opening 48 for acceptance to the main body of trocar 40. Sufficient steady forward pressure by hand on handle 49 causes rod 42 to eject drug delivery device 30 from chamber 47 through hollow needle opening 48 into a preselected body environment.

Figure 5:
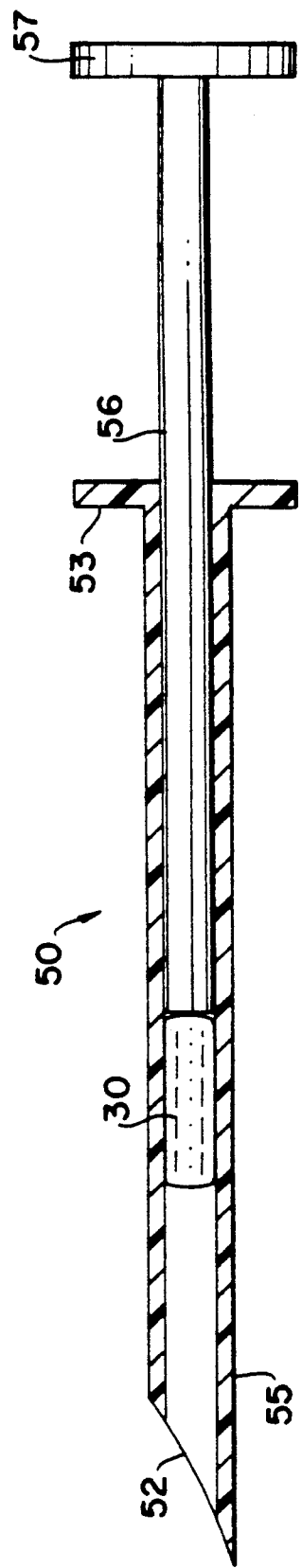
FIG. 5 is a side elevation view partly in cross section of a disposable plastic needle-like instrument with a drug delivery device within its barrel for the subcutaneous deposition by perforation to a preselected body part of an animal.

In FIG. 5 there is shown a simplified, disposable plastic trocar-type device 50 comprised of barrell 55 with hollow needle opening 52 at one end and retaining plate 53 at its other end, and rod 56 slidably received within the core of barrel 55. Trocar 40 and 50 can be fabricated of any material commonly used to inject a drug into an animal. After perforating the animal at the preselected site, sufficient steady forward hand pressure applied to handle 57 will cause rod 56 to eject drug delivery device 30 (contained in the core of the barrel) through needle opening 52 into the body environment. Alternatively, barrel 55 can be retracted from the body site by applying outward hand pressure on retaining plate 53 while maintaining rod 56 in its original fixed position with sufficient holding pressure. As barrel 55 is slowly retracted drug delivery device 30 will be deposited into the body site thorugh needle opening 52.

The novel drug delivery devices, in a preferred aspect, are highly useful in the delayed/sustained and the immediate/sustained release of active agents to animals, e.g., humans, sheep, dogs, cats, turkeys, cattle, etc. "Delayed/sustained release" is defined as delaying the release of an active agent until after placement in a delivery environment, followed by a sustained, preferably zero-order, release of the agent at a later time. "Immediate/sustained release" is defined as the commencement of the release of an active agent immediately or soon thereafter after placement in a delivery environment, followed by sustained release of the active agent. Other applications of the present invention include controlled delivery in industrial, agricultural and domestic settings.

In preferred aspects, the drug delivery devices of the invention are small cylindrically shaped implants containing within their core an active agent such as a macromoleculer composition discussed herein, and optionally, a pharmaceutically acceptable carrier. The membrane thickness (between the interior and exterior and exterior surfaces) of the implant is substantially uniform, and serves as a rate-limiting barrier for the release of the contained agent. Such implants can be plasticized or hydrated and reshaped into other geometrically shaped articles for use in various medical applications. The hydrophilic implant as a xerogel, readily absorbs water. In a hydrated state it is referred to as a hydrogel. In either form, it is biocompatible and non-toxic to the host and non-biodegradable. It is, of course, water-swellable and water-insoluble. When the hydrogel attains its maximum level of hydration, the water content of the hydrogel is referred to as "equilibrium water content". The percent water content of the hydrogel (any state of hydration) is determined as follows:

$$\frac{\text{Weight of Hydrogel} - \text{Weight of Dry Polymer (Xerogel)}}{\text{Weight of Hydrogel}} \times 100$$

In the manufacture of the cylindrically-shaped device, several factors are considered. The release profile (delay time, release rate, and duration) is determined; the hydrophilic polymeric material is identified; and the diffusivity of the active agent through it (as a rate-limiting membrane) is measured. The hydration profile of the rate-limiting membrane for a given active agent may be readily determined by preparing a film of the selected polymer and subjecting it to a diffusion study, using a two compartment vertical glass cell, as is well known in the art.

The diffusion coefficient and the water content at which diffusion begins (i.e., below which substantially no diffusion occurs—hereinafter "%$H_d$") are determined. A series of membranes is prepared from various polymers. The membranes are then hydrated to their capacity and their equilibrium water contents are measured. The fully hydrated membranes are placed in the two-compartment, vertical glass cells to measure and plot the diffusion of the macromolecular composition through the membrane materials at the various equilibrium water contents. The equilibrium water content of the most hydrated membrane through which no diffusion is detected (i.e., none of the active agent diffuses into the receptor cell) is the %$H_d$ for the system being tested. This can be accomplished by plotting a curve of the permeability vs. equilbrium water content.

The permeability results (diffusion coefficients) are obtained according to Fick's First Law of Diffusion, by use of the equation:

$$\frac{dQ}{dt} = \frac{APC_d}{1}$$

wherein dQ/dt is the flux through the membrane material ($\mu$g/hr); it is measured as the slope of the linear part of the curve of cumulative transport versus time; wherein A is the area of the membrane (cm$^2$); wherein P is the membrane's permeability coefficient (cm$^2$/hr), or $DK_d$, wherein D is the diffusivity of the membrane (cm$^2$/hr), and $K_d$ is the partition coefficient for the membrane/donor solution; wherein 1 is the membrane thickness as measured at the end of the experiment (cm); and wherein $C_d$ is the concentration of the donor solution ($\mu$g/cm$^3$).

The release delay profile is then determined. Another series of polymeric membranes can be prepared, again varying the amounts of crosslinker and monomers. These membranes are then hydrated, but only partially, i.e., to a water content less than or equal to %$H_d$. The partially hydrated membranes are placed in two-compartment vertical glass cells to measure and plot the diffusion of the active compound through the membranes versus time. Buffer solutions for the donor and receptor cells may be selected to contact the partially hydrated membranes and further hydrate them at approximately the same rate at which they will hydrate in the delivery environment. The time between commencement of the diffusion study, i.e., addition of the active agent to the donor cell, and the detection of a pharmaceutically effective concentration of the active agent in the receptor cell is the release delay time for that combination of polymer and initial percent hydration.

In order to determine the physical dimensions of the cylindrically-shaped device, the total amount of active agent to be delivered must be determined. This is the product of the desired daily dosage and the duration of delivery.

The volume of the cylindrical reservoir (core) of a cylindrically-shaped device is equal to $\pi r_i^2 h$ wherein $r_i$ is the radius of the reservoir and h is its height. The formula for steady state release from a cylinder is:

$$[dQ/dt] = [2\pi h DK_d C_d]/[\ln (r_o/r_i)]$$

wherein $r_o$ is the outside radius of the cylindrical device; and wherein $C_d$ is the concentration of drug in the donor solution, i.e., the carrier. Steady state release is obtained when $C_d$ is maintained at saturation. The thickness of the membrane needed for the desired sustained release is, therefore, $r_o - r_i$.

One aspect of the invention relates to a delivery device capable of delayed/sustained release of therapeutic dosages of an active agent into an aqueous delivery environment. The expression "active agent" ("active compound") as used herein broadly includes any compound or mixture thereof that can be delivered from the delivery device to produce a beneficial and useful result. The active agents whether in solid or liquid form will have sufficient solubility or miscibility in an aqueous system to render them capable of being released through the tailored-made hydrogel membranes into the delivery environment. The expressions "drug" including "macromoleculer drug" as used herein include any physiologically or pharmacologically active substance that produces a localized or a systemic effect in animals. The active drugs that can be delivered include inorganic and organic drugs that act on the central nervous system, psychic energizers, tranquilizers, anticonvulsants, muscle relaxants, antiparkinson, analgesic, anti-inflammatory, anesthetic, antispasmodic, muscle contractants, anti-microbials, anti-malarials, hormonal agents, sympathomimetic, cardiovascular, diuretics, antiparasitic and the like.

The expression "macromoleculer drug" as used herein is intended to include drugs, i.e., a substance that affects the activity of a specific bodily organ or function, having a molecular weight upwards to 25,000 and more, preferably greater than 1,000, preferably still from about 1,000 to about 25,000. Some drugs, e.g., steroids, anabolic agents and insulin, are characterized by a tendency toward aggregation with a resulting decrease in solubility. Suitable drugs include but are not limited to endocrine agents, chemotherapeutic agents, antibiotics, antidrug addiction agents, oncological treating agents, antiftingal agents, anti-pulmonary disfunction agents, enzymes and macromolecular proteins affecting the central nervous system. Preferred macromolecular drugs include native and recombinant bioactive proteins and analogs thereof, such as (1) growth hormones and analogs thereof, (2) insulin and insulin-like growth factors such as somatomedins and analogs thereof and (3) other pituitary derived hormones such as prolactin and analogs thereof.

Hormonally active polypeptides are those peptides that have a specific regulatory effect on the activity of a certain body organ. Generally, they are secreted by an endocrine gland. Some peptides not secreted by an endocrine gland, however, exhibit a specific regulatory effect on a body organ and therefore are also classified as hormonally active compounds. Synthetically prepared analogs of naturally occurring hormonally active polypeptides and pharmaceutically acceptable salts of the naturally occurring hormones and their synthetic analogs that retain the same type of activity as their parent also are useful in the invention.

Hormonally active polypeptides comprise a diverse group of proteins but because of their functional specificity they can conveniently be grouped into discrete classifications by physiological effect. Each protein group generally regulates one specific physiological function by interacting only with the organ or organs directly affecting that function. For example, luteinizing hormone-releasing hormone (LH-RH)-active polypeptides act on the anterior pituitary gland to effect release of hormones that affect the activity of reproductive organs. Growth hormones act on the liver causing it to release somatomedin, the peptide factor responsible for skeletal growth. Thymosin and thymically active peptides interact with the autoimmune system, enhancing the ability of the body's immune system to combat disease. The naturally occurring luteinizing hormone-releasing hormone polypeptide and the synthetic analogs thereof are of particular interest for use in the novel delivery device.

The naturally occurring LH-RH peptide is produced in the hypothalmic region of the brain and controls the reproductive cycle of mammals by acting on the anterior pituitary gland to affect release of luteinizing hormone ("LH") and follicular stimulating hormone ("FSH"), which in turn act on the gonads to stimulate the synthesis of steroid hormones and to stimulate gamete maturation. The pulsatile release of LH-RH thereby controls the reproductive cycle in mammals. Additionally, LH-RH has effects in the placenta, in releasing human chorionic gonadotropin ("HCG"), and directly on the gonads.

Agonist analogs of LH-RH are useful for the control of fertility by two mechanisms of action. Low doses of LH-RH analogs can stimulate ovulation and are useful in the treatment of hypothalmic and ovulatory infertility. Additionally, they can be used for hypogonadal conditions and impotence, and for stimulating spermatogenesis and androgen production in the male.

Paradoxically, larger doses of highly potent and long-lasting analogs of LH-RH have an opposite effect, blocking ovulation in the female and suppressing spermatogenesis in the male. Related to these effects is a suppression of normal circulating levels of sexual steroids of gonadal origin, including reduction in accessory organ weight in the male and female. In domestic animals this paradoxical effect promotes weight gain in a feed-lot situation, stimulates abortion in pregnant animals and, in general, acts as a chemical sterilitant. A frill list of the paradoxical high dose effects of LH-RH and its analogs is set out in U.S. Pat. No. 4,234,571.

There is also a group of LH-RH analogs termed antagonists. These polypeptides have the paradoxical effect shown by LH-RH agonists, but at low dose levels relative to naturally occurring LH-RH. Such compounds are included within the scope of the invention.

The natural LH-RH peptide is a hydrophilic decapeptide comprised of naturally occurring amino acids (which have the L-configuration except for the achiral amino acid glycine). Its sequence is as follows: (pyro)-Glu-His-Trp-Ser-Tyr-Gly-Leu-Arg-Pro-Gly-NH$_2$.

Another group of hormonally active polypeptides of interest herein are mammalian growth hormones. Growth hormones may be considered generally to be any substance which stimulates growth of the mammal when appropriately administered. The compounds of interest herein are those polypeptides secreted by the anterior pituitary gland, which exert an influence on protein, carbohydrate and lipid metabolism and control the rate of skeletal and visceral growth. Generally, growth hormones are species specific polypeptides with molecular weights falling between 22,000 and 24,000 daltons. In several species, for example, humans and cattle, the growth hormone also possesses some of the activities of lactogenic hormones.

Until recently, the availability of human growth hormone ("hGH") has been limited to that which could be extracted from the pituitary gland of human cadavers. However, recombinant DNA techniques have recently made it possible to produce biologically active hGH from bacteria in relatively substantial quantities.

Also contemplated are short-chain peptides of 10–13 amino acids that demonstrate thymic activity. A number of substances are known which, when administered to animals, enhance the ability of an organism's immune system to combat disease. Among these substances are crude extracts of myobacteria, glycopeptides and modifications of glycopeptides which are derived therefrom, and "thymosins," a family of hormones secreted by a thymosin gland.

The macromolecular compositions of this invention will be present in the delayed/sustained release compositions in varying amounts, depending upon the effect desired.

Treatment of infertility with synthetic LH-RH peptides requires a low level of drug, while reduction of fertility and related effects requires a large dose relative to the activity of naturally occurring LH-RH. For LH-RH agonist fertility control it is desired to release the drug at such a rate that the subject will receive between about 0.01 and 100 μg/kg body weight per day, preferably between 0.1 and 5.0 μg/kg body weight per day.

Human growth hormone quantities necessary to effect normal growth have not been precisely defined. HGH administered in amounts of about 0.1 to 10.0 Units (as defined by convention—based on biological activity for the particular hormone preparation—e.g., in one instance there are about 1.4 Units per mg of protein) per day based on body weight will effect increased linear growth in hGH-deficient children. A recent study by D. Rudman, et al. [J. Clin. Endocrine Metabolism, 49: 92–99 (1979] has demonstrated the onset of increased linear growth in children known to be deficient in hGH and showing shorter stature and lower than average growth rates for their age groups by the administration of 0.3 to 3.0 Units of hGH per day.

Bovine, sheep or horse growth hormone may be administered on a daily basis in an amount anywhere between 5–100 mg/day. The dose may vary depending upon the activity of the growth hormone, the species, and the size of the animal.

Thymic peptides can be administered in the range of from about 10 ng/kg/day to about 20 mg/kg/day, preferably from about 100 ng/kg/day to about 5 mg/kg/day. Expressed in alternative terms for an average (70 kg) adult human subject, this would be from 700 ng/day to 1.4 g/day, preferably from 7 mg/day to 350 mg/day.

The amount of active agent employed will depend not only on the desired daily dose but also on the number of days that dose level is to be maintained. While this amount can be calculated empirically, the actual dose delivered is also a function of any interaction with materials and the carrier, if employed in the device.

In various embodiments, the novel drug delivery device may contain a pharmaceutically acceptable carrier which may be in the form of suspending media, solvents, aqueous systems, and solid substrates or matrices.

Suspending media and solvents useful as the carrier include, for example, oils such as silicone oil (particularly medical grade), corn oil, castor oil, peanut oil and sesame oil; condensation products of castor oil and ethylene oxide combining about 30 to 35 moles of ethylene oxide per mole of castor oil; liquid glyceryl triesters of a lower molecular weight fatty acid; lower alkanols; glycols; polyalkylene glycols.

The aqueous systems include, for example, sterile water, saline, dextrose, dextrose in water or saline, and the like. The presence of electrolytes in the aqueous systems may tend to lower the solubility of the macromoleculer drug in them.

The solid substrates or matrices include, for example, starch, gelatin, sugars (e.g., glucose), natural gums (e.g., acacia, sodium alginate, carboxymethyl cellulose), and the like.

The carrier may also contain adjuvants such as preserving, stabilizing, wetting and emulsifying agents, and the like.

The hydrating liquid useful in the practice of the invention is typically a liquid simulating the environment in which the active compound will be released, e.g., body fluid, sterile water, tear fluid, physiological saline solution, phosphate buffer solution, and the like. While liquids other than water are useful as the hydrating liquid, the degree to which a hydrophilic membrane is bydrated is referred to as its "water content".

The devices of the invention(s) result in sustained release of the macromolecular drugs over extended periods of time. This time period may range from several days to a few years, for example, from one week to 3 years depending on the desired administration regimen. Preferably, the release time will be about 1 week to 18 months, and longer, it being understood that this time factor is a variable depending on the rate-releasing membrane of choice, its interconnecting pore structure, the active compound of choice, the solubility of the active compound in the liquid medium, and other considerations well known to those skilled in the art.

In operative Examples 2–20, hydrophilic cartridges were prepared by the rotational casting of polymerizable material in a tubular mold. The internal radius of the tube was approximately 1.2–1.3 mm. The tube was rotated about its longitudinal axis which was maintained parallel to the ground. Rotational speeds were of the order of 2,150 rpm, though greater or lesser speeds could be used, e.g., 1,000 rpm or less to 2,500 rpm and more. The tubes were fabricated of polyethylene or polypropylene. When the polymerizable mixture within the spinning tube stabilized to the predetermined shape, U.V. light at a distance of less than one foot was then directed at the spinning tube for several minutes, e.g., about 7 minutes, to polymerize the mixture to the shaped product. The shaped product was cured and annealed as follows:

| Thermal Cure: | 60 minutes at 65° C. |
| --- | --- |
| Postcure: | 30 minutes at 95° C. |
| Annealing: | 30 minutes at 115° C. with gradual cooling to about 25° C. |

After shaping and polishing the closed end of the cartridge to an oval-like cylindrical profile, there was obtained small cylindrically-shaped objects having smooth, unscored cylindrical surfaces. The dimensions of the cartridges were as follows: internal radius 0.8 mm; external radius 1.3 mm; length 10 mm. In preferred embodiments, small drug delivery devices can be implanted subcutaneously in an animal by perforation. Such devices are characterized by a length of 10–12 mm, or less (e.g., 6–9 mm), an external diameter of 2–2.5 mm, or less (e.g., 1.5–1.9 mm), and an internal diameter of 1–1.2 mm, or less (e.g., 0.6–0.9 mm). The dimensions of the cartridge can vary outside of the limits stated above depending, in particular, on the medical application involved. Animals such as sheep, cows, goats, cattle, and large animals, in general, can tolerate implantation by perforation of larger dimensional drug delivery devices. Implantation can be effected by other means, e.g., open surgery.

Smooth, unscored cylindrically-shaped objects of varying lengths, e.g., up to 25 cm and longer, can also be prepared in accordance with the teachings herein. Such objects, in a hydrated state or plasticized with a non-toxic, biocompatible material, can be formed into desired shapes, e.g., a ring shape, for use as pessaries, surgical implants, etc.

Whenever the polymer is designated herein by "%" as in 50% HEMA/49.5% HPMA/0.5% TMPTMA, the meaning intended is "% by weight".

EXAMPLE 1

A monomeric mixture comprising 90% 2-hydroxyethyl methacrylate, 5% methyl methacrylate, and 5% ethylene glycol dimethacrylate was prepared. All the monomers were previously purified by vacuum distillation. To the resulting mixture 0.2% benzoin methyl ether was added and stirred until dissolved. The mixture was deoxygenated by bubbling nitrogen through it for 10 minutes. To avoid premature polymerization the mixture was shielded from light. One end of a polypropylene tube (65 mm in length and $D_i$ of 2.5 mm) was plugged with a silicone sealant; the other end of the tube was sealed with a plug made by injecting a small amount of the above mixture which was cured under a UV lamp for 5 minutes. Using a syringe filled with said mixture, the silicone plug was punctured and the tube was filled with the mixture to a height of about 10 mm from the top. The tube was inserted in a lathe collet and spun (spinning axis parallel to the ground) at about 2,200 rpm. The centrifugal force created by the spinning tube caused the radially outward displacement of the mixture to assume a predetermined hollow cylindrical liquid configuration (i.e., a hollow tube of polymerizable liquid mixture). The spinning tube was then exposed to U.V. light for 7 minutes to polymerize the "liquid tube" to a solid hydrophilic tube (cartridge). The cartridge within the polypropylene tube was post-cured for 14 hours at 65° C., followed with an additional 40 minutes at 105° C., and annealed at 116° C. for 40 minutes, and then slowly cooled to 22° C.

The cartridge was ejected from the tube, inspected for defects, and cut to a length of 30 mm. There was obtained a precisely dimensioned plastic cartridge fabricated of crosslinked heterogeneous 90% HEMA/5% MMA/5% EDGMA copolymer characterized by recurring hydrophilic and hydrophobic units. The weight of the cartridge was recorded. It was then filled with LHRH-13 (luteinizing hormone releasing hormone) by tightly packing it to a 20 mm height. The filled cartridge was weighed again to determine the weight of LHRH-13. The top of the drug was covered with a square of teflon tape. The remainder of the empty space of the cartridge was filled with the aforesaid monomeric mixture. Part of the cartridge containing LHRH-13 was covered with aluminum foil. The cartridge was then placed in the lathe and spun slowly under a UV lamp for 5 minutes to effect polymerization of the mixture. Postcuring of the polymer plug was effected by maintaining the cartridge at 50° C. for 18 hours. The end product was a drug delivery device.

The equibrium water content of the polymer cartridge was determined to be 28%. The drug delivery device was then subjected to an elution study in saline solution (10 ml per device) that was adjusted to pH 7 and preserved with 200 ppm of sodium azide. Samples were incubated in a shaker water bath at 37° C. The eluants were analyzed by HPLC on μBondapak C18 column at 7 day intervals. The elution rate of LHRH-13 from the device was determined to average approximately 13 μg/day over a one year period.

EXAMPLES 2-20

Following the general procedure described in the discussion of FIG. 1, several homogeneous hydrophilic cartridges were prepared using polyethylene tubes having a length of 48 mm and an internal diameter ($D_i$) of 2.6 mm. Each end of the tube were stoppered with a Delrin ® plug. Using a 250 μl syringe there was introduced 140 μl of polymerizable material into the open end of each tube. The remaining air space in the tube was gently purged with nitrogen using a syringe needle. Each tube, positioned, locked and sealed on the "Levin" lathe as described aforesaid was rotated with its longitudinal axis parallel to the ground at 2,150 rpm until the polymerizable material stabilized to form a predetermined hollow cylindrical liquid configuration within the tube. U.V. light was then directed at the spinning tube for 7 minutes thereby causing the hollow cylindrical liquid configuration to polymerize to a solid configuration. The resulting shaped polymer was subjected to a thermal cure for 60 minutes at 65° C., a post cure for 30 minutes at 95° C., and an annealing treatment for 30 minutes at 115° C. followed by gradual cooling to ambient temperature (25° C.). Pertinent data including the equilibrium water content of the cartridges are set forth on Table I infra.

TABLE 1

| Example | HEMA %[1] | HPMA %[2] | X-L %[3] | Catalyst[4] | E.W.C. %[5] |
|---|---|---|---|---|---|
| 2 | 99.5 | 0 | 0.5[6] | 0.4 | 37.5 |
| 3 | 89.0 | 10 | 1.0[7] | 0.4 | 35.2 |
| 4 | 79.0 | 20 | 1.0[7] | 0.4 | 33.6 |
| 5 | 70.0 | 29.5 | 0.5[6] | 0.4 | 33.1 |
| 6 | 60.0 | 39 | 1.0[7] | 0.4 | 30.5 |
| 7 | 50.0 | 49.5 | 0.5[6] | 0.4 | 30.1 |
| 8 | 45.0 | 54.5 | 0.5[6] | 0.4 | 29.5 |
| 9 | 40.0 | 59.5 | 0.5[6] | 0.4 | 28.7 |
| 10 | 40.0 | 59.2 | 0.8[6] | 0.4 | 28.2 |
| 11 | 35.0 | 64.5 | 0.5[6] | 0.4 | 27.7 |
| 12 | 30.0 | 69.5 | 0.5[6] | 0.4 | 27.6 |
| 13 | 30.0 | 69.0 | 1.0[6] | 0.4 | 27.3 |
| 14 | 30.0 | 68.5 | 1.5[6] | 0.4 | 25.7 |
| 15 | 30.0 | 68 | 2.0[6] | 0.4 | 25.1 |
| 16 | 25 | 74.5 | 0.5[6] | 0.4 | 26.3 |
| 17 | 20 | 79.5 | 0.5[6] | 0.4 | 26.0 |
| 18 | 10 | 89.5 | 1.0[6] | 0.4 | 24.5 |
| 19 | 10 | 89 | 1.0[7] | 0.4 | 24.1 |
| 20 | 0 | 99.5 | 0.5[6] | 0.4 | 22.9 |

[1]% by weight 2-hydroxyethyl methacrylate
[2]% by weight 3-hydroxypropyl methacrylate
[3]X-L represents % by weight of crosslinker
[4]0.3% by weight of benzoin methyl ether plus 0.1% by weight of bis(4-t-butylcyclohexyl) peroxydicarbonate
[5]Equilibrium water content
[6]Trimethylolpropane trimethacrylate
[7]Ethylene glycol dimethacrylate

EXAMPLES 21-27

The release rates in vitro of LHRH-13 and LHRH-40 into an aqueous medium maintained at about 37° C. from several delivery devices (cylindrically shaped implants) sealed with a plug of polyHENU were determined. The polyHENU plug had an equilibrium water content value of 37.5% (at approximately 25° C.). The aqueous medium ("sink") was monitored every 7 days and the quantity of LHRH released from the implant was calculated to give average rates on a per day basis. All LHRH release data were normalized to a standard implant length of 20 mm. The cartridges used in the fabrications of the implants were prepared in the manner set forth in various preceding examples. The correlation of the cartridges and the implants is shown below:

TABLE II

| Implant[1] | Cartridge[1] | HPMA[2] | Polymer[3] | Figure |
|---|---|---|---|---|
| 21 | 20 | 99.5 | 0/99.5/0.5 | 7 |
| 22 | 11 | 64.5 | 35/64.5/0.5 | 8 |
| 23 | 9 | 59.5 | 40/59.5/0.5 | 9 |

TABLE II-continued

| Implant[1] | Cartridge[1] | HPMA[2] | Polymer[3] | Figure |
|---|---|---|---|---|
| 24 | 7 | 49.5 | 50/49.5/0.5 | 10 |
| 25 | 6 | 39 | 60/39/1[4] | 11 |
| 26 | 5 | 29.5 | 70/29.5/0.5 | 12 |
| 27[5] | 2 | 0 | 99.5/0/0.5 | 13 |

[1]See Example.
[2]Weight % HPMA units in polymer.
[3]Make-up of polymer, % by wt. HEMA/HPMA/TMPTMA.
[4]EGDMA employed as the crosslinker in lieu of TMPTMA.
[5]Implant packed with LHRH-40; in Example 21-26 the implants were packed with LHRH-13.

EXAMPLES 28–38

Eleven cartridges were prepared from polymerizable monomeric mixtures comprising HEMA and/or HPMA and crosslinker. The equilibrium water content value (at ambient temperature, approximately 25° C.) were determined for each cartridge (y axis) and plotted against the weight percent of HPMA units in the polymer matrix (x axis). The data shown in FIG. 6 illustrates the linear relationship when these two factors are plotted. The pertinent data are set forth below in Table III.

TABLE III

| Example | % HPMA Unit in Polymer[1] | E.W.C. %[2] |
|---|---|---|
| 28 | 0 | 37.5 |
| 29 | 29.5 | 32.8 |
| 30 | 49.5 | 30.2 |
| 31 | 54.5 | 29.5 |
| 32 | 59.5 | 28.4 |
| 33 | 64.5 | 27.7 |
| 34 | 69.5 | 26.9 |
| 35 | 74.5 | 26.3 |
| 36 | 79.5 | 25.8 |
| 37 | 89.5 | 24.5 |
| 38 | 99.5 | 22.9 |

[1]Weight % 3-hydroxypropyl methacrylate units in HEMA/HPMA polymer using 0.5 wt. % TMPTMA.
[2]% Equilibrium Water Content.

The crosslinked homogeneous HEMA/HPMA copolymers containing from about 30 to 75 weight % of HPMA units in the polymer chain are particularly preferred as biocompatible, non-biodegradable, non-toxic hydrogel material for use in drug delivery devices, especially for the sustained release of LHRH and its analogs, as exemplified by LHRH-13, to the delivery environment. The homogeneous copolymers have extremely low interfacial free energy values and, in the practice of various aspects of the invention(s), body implants fabricated of such copolymers are biologically compatible with the body environment as evidenced by a lack of a thick, fibrous capsula on the implant. Homogeneous copolymers outside the above-stated preferred range are also within the scope of the inventions described herein, e.g., 90–10% HPNU/10–90% HENU copolymers.

EXAMPLE 39

Figure 14:
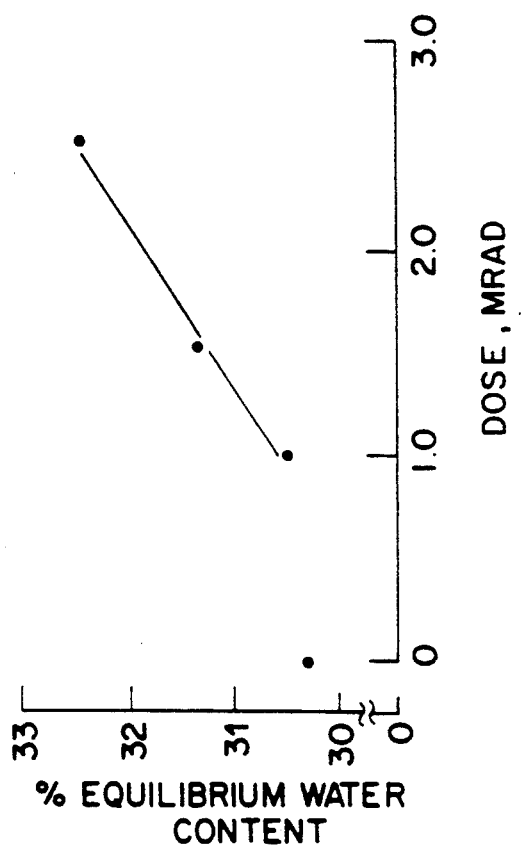
FIG. 14 is a graph showing the increase in equilibrium water content of a cylindrically-shaped implant of crosslinked hydrophilic 50% HEMA/49.5% HPNU polymer with increasing doses (in megarad) of irradiation over an eight hour period.
Figure 13:
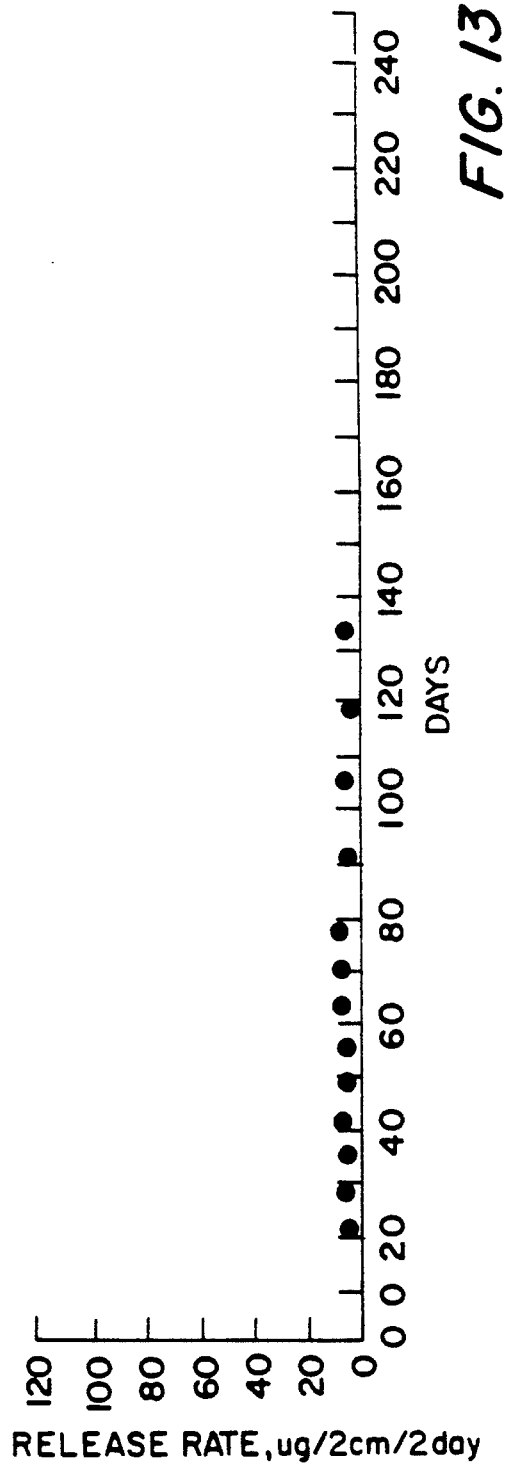
Figure 15:
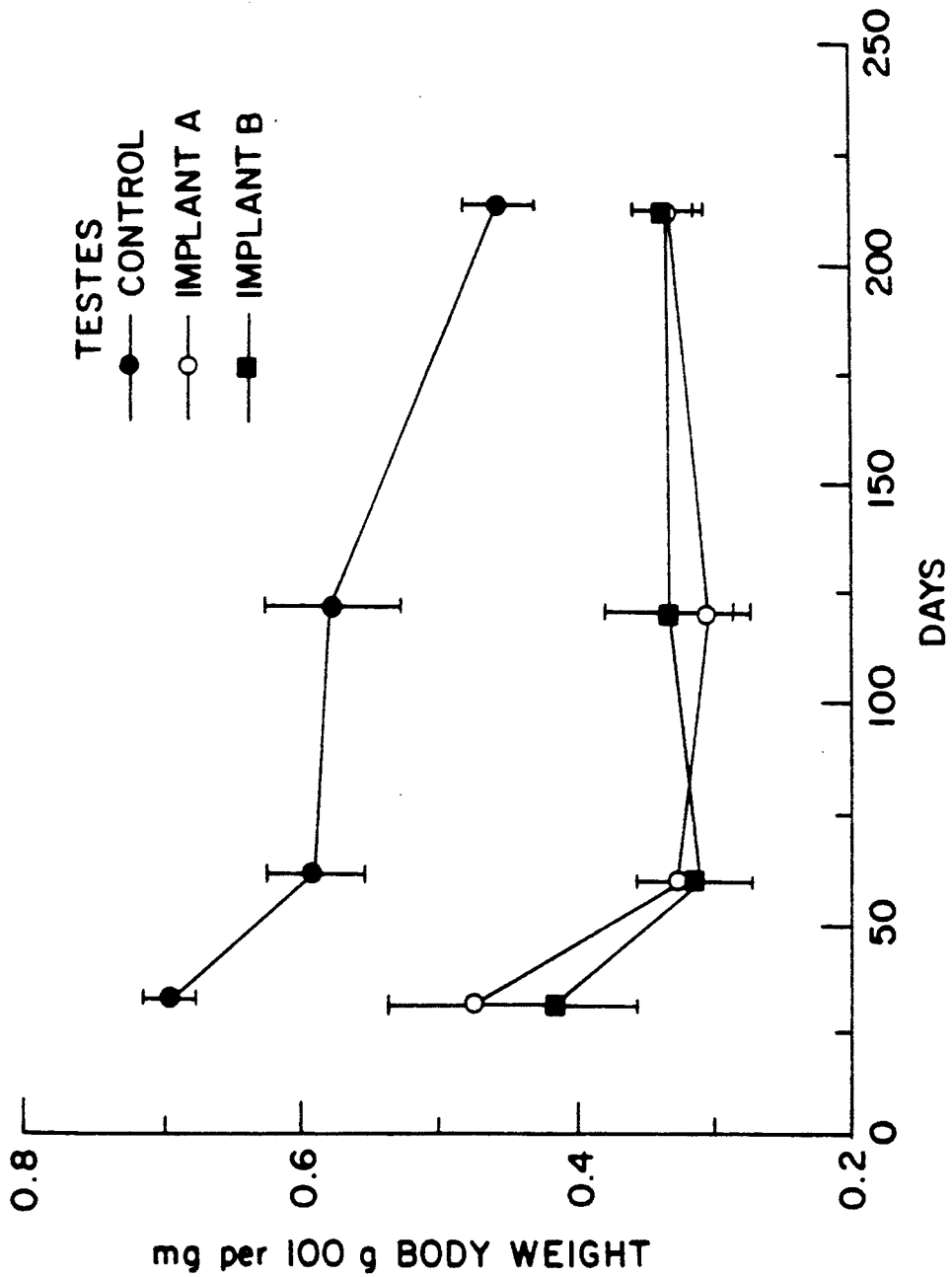
Figure 16:
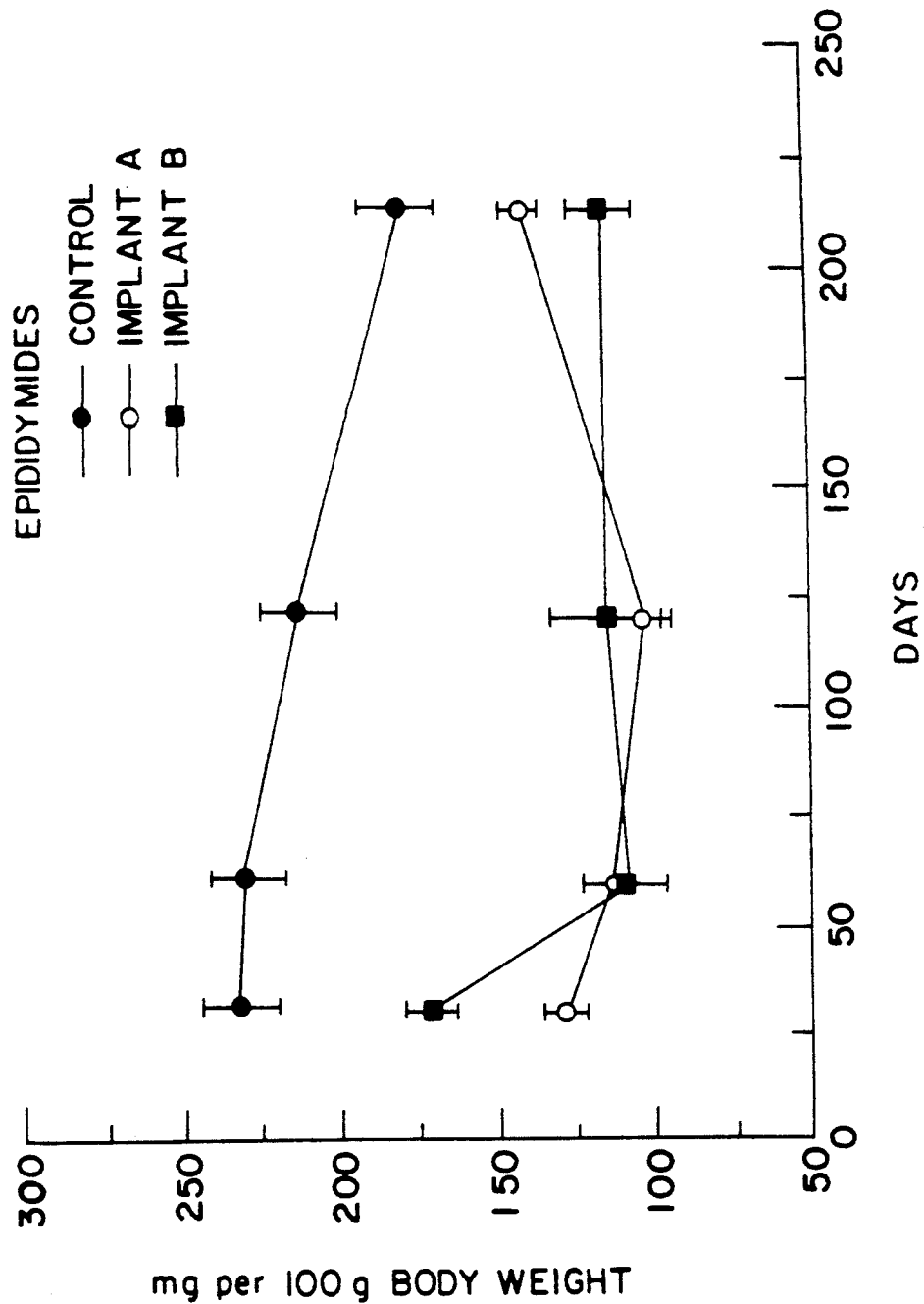

A 50% HEMA/49.5% HPMA/0.5% TMPTMA crosslinked polymer with an initial equilibrium water content of 30.2% was subjected to increasing doses of gamma-irradiation (in megarads) over an 8 hour period. FIG. 14 shows that % equilbrium water content of the polymer increased in a linearly relationship with increasing doses of irradiation. Test data confirmed that the release rate of LHRH-13 from hydrogel implants irradiated with 2.5 megarads was greater than that obtained from hydrogel implants irradiated with 1.0 megarads over similar periods.

EXAMPLES 40–43

Several cylindrically-shaped delivery devices designated as Implant A and Implant B, packed with LJiRH-13 as described previously, were prepared for testing in rats to ascertain the effect on suppression of the testes and accessory sex glands. Implant A is fabricated of 50% HEMA/49.5% HPMA/0.5% TMPTMA and Implant B of 40% HEMA/59.5% HPMA/0.5% TMPTMA Implant A was implanted in one group of rats and Implant B was implanted in a second group of rats. Periodically, a designated number of rats were sacrificed and their testes, epididymides, ventral prostate, and seminal vesicles were weighed. The amount of LHRH-13 released from both Implants A and B were sufficient to suppress testicular and accessory sex glands and weights. In all instances, the weight suppressions exceeded that of the controls.

In FIGS. 15-18 there are shown graphically the weight of the testes, epididymides, ventral prostate, and seminal vesicles respectively, in mg per 100 g of rat weight vs. number of days. The rats were sacrificed at intervals of approximately 30, 60, 120 and 215 days.

Upon removal of the implants from the rats a few implants showed slight mineralization ascertained to be approximately calcium.

EXAMPLE 44

Cartridges fabricated from 4 different formulations were prepared. The data are set out in Table IV:

TABLE IV

| Formulation | HEMA % | HPMA % | TMPTMA % | BME %[1] | P-16%[2] |
|---|---|---|---|---|---|
| 1 | 50 | 49.2 | 0.8 | 0.2 | 0.1 |
| 2 | 40 | 59.2 | 0.8 | 0.2 | 0.1 |
| 3 | 50 | 49.8 | 0.5 | 0.2 | 0.1 |
| 4 | 40 | 59.5 | 0.5 | 0.2 | 0.1 |

[1]Benzoin methyl ether.
[2]Bis(4-t-butylcyclohexyl) peroxydicarbonate.

A set of five cartridges (cylindrical wall thickness of 0.5 mm) were made from each of the 4 formulations noted above. The overall dimensions of the cartridges were equal. To each set of five cartridges there was added Poly B TM -411, a solid hydrophilic blue dye manufactured by Dynapol Co. and sold by Sigma Aldridge, Cat. No. 86172-3, and Sweet and Low ® Brand sugar substitute as an inert filler. The cartridges were sealed with a plug of crosslinked polyHEMA described previously. Each implant was then hydrated at room temperature in separate vessels containing 0.9 weight percent saline solution.

The blue dye, in solution, was unable to diffuse through the hydrogel membrane since its molecular size exceeded the permeability of the membrane.

The core of the 5 implants of each formulation swelled noticeably. By the third day the cylindrical wall of the five implants of Formulation 1 had burst. By the fourth day the cylindrical wall of the five implants of Formulation 2 implants had burst. By the fifth day the cylindrical wall of the five implants of Formulation 3 had burst. With respect to the Formulation 4 implants there remained 2 implants which were still intact on the seventh day, the cylindrical wall of the remaining 3 implants having burst on the sixth day. The bursting effect was evident by the dye seeping through the wall of the cylinder into the saline solution. In every instance, no leakage or bursting occurred at the interface of the polymer plug and the internal surface of the cartridge. The overall mechanical properties such as tensile strength, modulus, and elasticity were noticeably better with the implants of Formulation 3 and Formulation 4. This phenomenon could be attributable to the lesser concentration of tri-ethylenically unsaturated crosslinker employed.

What is claimed is:

1. A method for centrifugally casting a biocompatible, non-biodegradable, water-swellable, water-insoluble, hydrophilic plastic cartridge of uniform wall thickness useful as a rate-limiting barrier in a drug delivery device which comprises:
   a. rotating a tube comprising a core of smooth uniform cylindrical surface, said tube containing a predetermined quantity of at least one polymerizable hydrophilic liquid monomer and closure means to prevent loss of said liquid monomer during rotation;
   b. maintaining the longitudinal axis of the rotating tube parallel to the ground and effecting the rotation at a speed sufficient to cause radially outward displacement of said liquid monomer to assume a cylindrically-shaped liquid cartridge having a predetermined configuration within said tube;
   c. subjecting the tube to polymerization conditions to convert said liquid state cartridge to a solid state hollow plastic cartridge of predetermined configuration; and
   d. recovering a biocompatible, non-degradable, water-swellable, water-insoluble, hydrophilic cylindrically-shaped plastic cartridge having walls of uniform thickness between its smooth external and internal cylindrical surfaces.

2. The method of claim 1 wherein said polymerizable liquid monomer comprises hydrophilic ethylenically unsaturated monomers and an agent to effect the catalysis thereof.

3. The method of claim 2 wherein the polymerization reaction is carried out in the presence of radiation and a catalyst therefor.

4. The method of claim 3 wherein said polymerizable liquid monomer contains benzoin methyl ether as an initiator and wherein said radiation is ultra-violet light.

5. The method of claim 2 wherein the outer portion proximal to the closed end of said cartridge is subjected to a shaving step thereby imparting a smooth oval shape to the cartridge.

6. The method of claim 5 wherein said cartridge is a xerogel.

7. The method of claim 6 wherein said cartridge is a hydrogel.

8. The method for the preparation of a delivery device for the sustained release of an active agent therefrom which comprises:
   a. introducing active agent, and optionally a pharmaceutically acceptable carrier, into a cylindrically-shaped reservoir of a biocompatible, non-biodegradable water-swellable, water-insoluble, cylindrically-shaped plastic cartridge, in an amount sufficient to provide extended sustained release of the active agent, said cartridge having smooth external and internal cylindrical surfaces and a uniform thickness between said surfaces;
   b. introducing at least one polymerizable liquid monomer into the upper portion of said reservoir in an amount to close the open end of the reservoir, said polymerizable liquid monomer having an equilibrium water content value in its polymerized state which exceeds the equilibrium water content value of said plastic cartridge; and
   c. polymerizing said polymerizable liquid monomer to effectively seal the opening of the reservoir with a plug of water-swellable, water-insoluble polymer to form a delivery device which give a predetermined release of the active agent.

9. The method of claim 8 wherein said plastic cartridge has a smooth, oval cylindrical shape.

10. The method of claim 8 wherein the outer portion of the delivery device distal to the plug of polymer is subjected to a shaping step to impart a smooth oval shape thereto.

11. The method of claim 8 wherein said active agent is a drug.

12. The method of claim 11 wherein said drug is a macromolecular composition having an average molecular weight upwards to about 25,000.

13. The method of claim 12 wherein said macromolecular composition includes native and recombinant bioactive proteins.

14. The method of claim 12 wherein said macromolecular composition is a hormonally active polypeptide.

15. The method of claim 12 wherein said macromolecular composition is luteinizing hormone-releasing hormone polypeptide.

16. The method of claim 12 wherein said macromolecular composition is a mammalian growth hormone or mammalian growth releasing hormone.

17. The method of claim 8 wherein said plastic cartridge is a xerogel.

18. The method of claim 8 wherein said plastic cartridge is a hydrogel.

19. The method of claim 8 wherein said plastic cartridge is a hydrogel at its equilibrium water content.

20. The method of claim 17 wherein said polymerizable liquid material comprises an homogenous mixture of ethylenically-unsaturated monomer and a water-soluble pore-forming agent.

21. As an article, a biocompatible, non-biodegradable, water-swellable, water-insoluble, hydrophilic plastic cartridge useful as a rate-limiting barrier in a drug delivery device capable of being implanted in an animal by perforation, said plastic cartridge characterized by an oval cylindrical shape at its closed end, smooth unscored internal and external cylindrical surfaces, and a uniform thickness between said surfaces.

22. The article of claim 21 wherein the plastic cartridge is in the state of a xerogel.

23. The article of claim 21 wherein the plastic cartridge is hydrated.

24. The article of claim 21 wherein the plastic cartridge is a polymer of 2-hydroxyethyl methacrylate.

25. The article of claim 24 wherein the internal cylindrical surface area proximal to the open end of the cartridge has been scored and treated with a mono- or polyhydric alcohol to enhance graft polymerization of polymerizable ethylenically unsaturated monomer thereto.

26. A delivery device for the sustained release of an active agent therefrom which comprises:
   a. biocompatible, non-biodegradable, water-swellable, water-insoluble, hydrophilic plastic cartridge having a cylindrically-shaped reservoir;

b. said cartridge characterized by (i) an oval outer cylindrical shape at one end thereof; (ii) smooth internal and external cylindrical surfaces; and (iii) a uniform cylindrical wall thickness;

c. sealant means for closure of the open end of said reservoir comprising a plug of biocompatible, non-biodegradable, water-swellable, water-insoluble, hydrophilic polymer having an equilibrium water content value greater than that of the plastic cartridge per se; and d. an active agent contained in the reservoir of the cartridge in an amount sufficient to provide a predetermined sustained release thereof over an extended period of time.

27. The delivery of claim 26 wherein said active agent is a drug.

28. The delivery device of claim 26 wherein said active agent is a macromolecular composition having a molecular weight of upwards to 25,000.

29. The delivery device of claim 26 wherein said plastic cartridge and said sealant means are in the zerogel state.

30. The delivery device of claim 26 wherein said plastic cartridge and said sealant means are in the hydrogel state.

31. The delivery device of claim 26 wherein said active agent includes native and recombinant bioactive proteins.

32. The delivery device of claim 31 wherein said active agent is a hormonally active polypeptide.

33. The delivery device of claim 32 wherein said active agent is luteinizing hormone-releasing hormone polypeptide.

34. The delivery device of claim 26 wherein said active agent is a mammalian growth hormone or mammalian growth releasing hormone.

35. The delivery device of claim 33 wherein said delivery device contains a pharmaceutically acceptable carrier admixed with the active agent.

36. A method for the implantation of a small cylindrically-shaped delivery device into an animal for sustained release of an active agent therefrom which comprises:

a. perforating the skin of an animal at a preselected site with an instrument comprising a hollow needle and the delivery device of claim 26;

b. injecting said delivery device through said hollow needle and depositing it subcutaneously at the preselected site; and c. withdrawing said needle from the animal.

37. The method of claim 36 wherein said active agent comprises native or recombinant bioactive proteins.

38. The method of claim 37 wherein said active agent is a luteinizing hormone-releasing hormone polypeptide.

39. The method of claim 38 wherein the delivery device comprises a cartridge in a zerogel state.

40. The method of claim 38 wherein the delivery device comprises a cartridge in a hydrated state.

41. A kit useful for the implantation by perforation of a drug delivery device in an animal for sustained release of a drug therefrom comprising:

a. the drug delivery device of claim 37;

b. delivery means to eject said drug delivery device to the delivery environment of an animal; and c. container means to house said delivery device and said delivery means in a sterile aqueous medium.

42. The kit of claim 41 wherein said delivery means comprises a small rigid hollow tube of uniform internal diameter having a needle-like opening at one end thereof, and a telescoping solid rigid rod slidably communicating with the internal surface of said tube, and wherein said drug delivery device positioned within said tube is proximity with one end of the rod for slidable ejection from said tube.

* * * * *

UNITED STATES PATENT AND TRADEMARK OFFICE
CERTIFICATE OF CORRECTION

PATENT NO. : 5,292,515
DATED : March 8, 1994
INVENTOR(S) : Daniel G. Moro, Petr Kuzma, and Harry Quandt It is certified that error appears in the above-identified patent and that said Letters Patent is hereby corrected as shown below:

Col. 2, line 54, delete "(HENU)" and insert thereof -- (HEMA) --.

Col. 2, line 60, delete "HESM" and insert thereof -- HEMA --.

Col. 6, line 57, delete "("HPNW")" and insert thereof -- ("HPMA") --.

Col. 7, line 17, delete "HENW" and insert thereof -- HEMA --.

Col. 7, line 36, delete "HPNU" and insert thereof -- HPMA --.

Col. 16, line 19, delete "frill" and insert thereof -- full --.

Col. 20, line 53, delete "polyHENU" and insert thereof -- polyHEMA --.

Col. 21, line 56, delete "HPNU" and insert thereof -- HPMA --.

Col. 21, line 56, delete "HENU" and insert thereof -- HEMA --.

Col. 22, lines 6-7, delete "LJiRH-13" and insert thereof -- LHRH-13 --.

Signed and Sealed this

Twenty-sixth Day of July, 1994

Attest:

BRUCE LEHMAN

Attesting Officer            Commissioner of Patents and Trademarks

UNITED STATES PATENT AND TRADEMARK OFFICE
CERTIFICATE OF CORRECTION

PATENT NO. : 5,292,515

DATED : March 8, 1994

INVENTOR(S) : Daniel G. Moro, Petr Kuzma, and Harry Quandt

It is certified that error appears in the above-identified patent and that said Letters Patent is hereby corrected as shown below:

Col. 25, claim 27, line 17, after "delivery" insert -- device --.

Col. 26, claim 41, line 27, delete "37" and insert therefor -- 26 --.

Signed and Sealed this

Eleventh Day of July, 1995

*Attest:*

BRUCE LEHMAN

*Attesting Officer*  *Commissioner of Patents and Trademarks*